US006541276B2

(12) United States Patent
Patel et al.

(10) Patent No.: US 6,541,276 B2
(45) Date of Patent: Apr. 1, 2003

(54) METHODS FOR SOLID-PHASE SYNTHESIS OF HYDROXYLAMINE COMPOUNDS AND DERIVATIVES AND COMBINATORIAL LIBRARIES THEREOF

(75) Inventors: Dinesh V. Patel, Fremont, CA (US); Khehyong Ngu, Palo Alto, CA (US)

(73) Assignee: Versicor, Inc., Fremont, CA (US)

( * ) Notice: Subject to any disclaimer, the term of this patent is extended or adjusted under 35 U.S.C. 154(b) by 0 days.

(21) Appl. No.: 08/958,638

(22) Filed: Oct. 27, 1997

(65) Prior Publication Data

US 2001/0053555 A1 Dec. 20, 2001

Related U.S. Application Data

(60) Provisional application No. 60/047,468, filed on May 23, 1997, and provisional application No. 60/029,788, filed on Oct. 28, 1996.

(51) Int. Cl.$^7$ .................. G01N 33/543; A61K 38/00

(52) U.S. Cl. ............... 436/518; 435/DIG. 22; 435/DIG. 34; 435/DIG. 49; 530/335

(58) Field of Search ............... 436/518; 514/645, 514/507, 575; 564/30; 435/DIG. 22, DIG. 34, DIG. 49; 530/335

(56) References Cited

U.S. PATENT DOCUMENTS

| | | | |
|---|---|---|---|
| 4,028,401 A | * | 6/1977 | Fessler et al. ............ 260/500 |
| 4,831,084 A | | 5/1989 | Mergler et al. |
| 4,908,405 A | | 3/1990 | Bayer et al. |
| 4,914,151 A | | 4/1990 | Mergler et al. |
| 5,268,384 A | | 12/1993 | Galardy |
| 5,510,510 A | | 4/1996 | Patel et al. |
| 5,523,430 A | | 6/1996 | Patel et al. |
| 5,545,568 A | | 8/1996 | Ellman |
| 5,552,419 A | | 9/1996 | MacPherson et al. |
| 5,831,004 A | | 11/1998 | Campbell et al. |
| 5,840,698 A | | 11/1998 | Campbell et al. |
| 5,929,278 A | | 7/1999 | Campbell et al. |
| 5,932,579 A | | 8/1999 | Campbell et al. |
| 5,990,112 A | | 11/1999 | Campbell et al. |
| 6,025,371 A | | 2/2000 | Gordeev et al. |

FOREIGN PATENT DOCUMENTS

| | | |
|---|---|---|
| EP | 423943 | 4/1991 |
| EP | 687691 | 12/1995 |
| EP | 0606046 | 10/1997 |
| WO | WO 95/24186 | 9/1995 |
| WO | WO 95/35276 | 12/1995 |
| WO | WO 96/00378 | 1/1996 |
| WO | WO 96/06074 | 2/1996 |
| WO | WO 96/25156 | 8/1996 |
| WO | WO 96/26223 | 8/1996 |
| WO | WO 96/26918 | 9/1996 |
| WO | WO 97/15557 | 5/1997 |

OTHER PUBLICATIONS

Nishino et al. Biochemistry, 1978, 17 (14), pp. 2846–2850).*
Knobler et al . Isr. J. Chem. 1970, 8(4), 639–45.*
Gordon et al. Journal of Medicinla Chemistry, vol. 37, No. 9, Apr. 1994, pp. 12331251.*
Levy, E. et al (1998). "Matrix Metalloproteinase Inhibiors: A Structure–Activity Study," *J. Med. Chem.* 41(2):199–223.
Chan et al., "Crystal Structure of the *Escherichia coli* Peptide Deformylase," *Biochem.*, 1997, 36:13904–13909.
Chang et al., "Methionine Aminopeptidase Gene of *Escherichia coli* is Essential for Cell Growth," *J. Bacteriol.*, 1989, 171:4071–4072.
Meinnel and Blanquet, "Characterization of the *Thermus thermophilus* Locus Encoding Peptide Deformylase and Methionyl–tRNA$_f^{Met}$ Formyltransferase," *J. of Bacteriol.*, 1994, 176:7387–7390.
Meinnel et al., "A New Subclass of the Zinc Metalloproteases Superfamily Revealed by the Solution Structure of Peptide Deformylase", *J. Mol. Biol.*, 1996, 262:375–386.
Meinnel et al., "Structure–Function Relationships within the Peptide Deformylase Family. Evidence for a Conserved Architecture of the Active Site Involving Three Conserved Motifs and a Metal Ion", *J. Mol. Biol.*, 1997, 267:749–761.
Ngu, K. et al, "A New and Efficient Solid Phase Synthesis of Hydroxamic Acids," *J. Org. Chem.*, 1997, 62:7088–7089.
Rajagopalan et al., "Peptide Deformylase: A New Type of Mononuclear Iron Protein," *J. Am. Chem. Soc.*, 1997, 119:12418–19.
Rajagopalan et al., "Purification, Characterization, and Inhibition of Peptide Deformylase from *Escherichia coli,*" *Biochem.*, 1997, 36(45):13910–13918.
Wei et al., "Continuous Spectrophotometric Assay of Peptide Deformylase," *Anal. Biochem.*, 1997, 250:29–34.
Albericio et al., "Preparation and Application of the 5–(4–(9–fluorenylmethyloxycarbonyl)aminomethyl–3, 5–dimethoxyphenoxy)–valeric acid (PAL) handle for the solid–phase synthesis of C–terminal peptide amides under mild conditions" *J. Org. Chem.* (1990) 55:3730–3743.
Albericio et al., "Hypersensitive acid–labile (HAL) TRIS- (alkoxy)benzyl ester anchoring for solid–phase synthesis of protected peptide segments" *Tet. Lett.* (1991) 32(8):1015–1018.

(List continued on next page.)

*Primary Examiner*—Padmashri Ponnaluri
(74) *Attorney, Agent, or Firm*—Morrison & Foerster LLP

(57) ABSTRACT

A novel method for generating hydroxylamine, hydroxamic acid, hydroxyurea, and hydroxylsulfonamide compounds is disclosed. The method involves the nucleophilic attack of an alkoxyamine on a suitable solid phase support. Techniques of combinatorial chemistry can then be applied to the immobilized alkoxyamine to generate a diverse set of compounds. Cleavage of the compounds from the support yields a library of hydroxylamine or hydroxylamine derivative compounds, which can be screened for biological activity (e.g., inhibition of metalloproteases).

7 Claims, 10 Drawing Sheets

OTHER PUBLICATIONS

Alexandratos et al., "Polymer–supported reagents: Application to separation science" *Ind. Eng. Chem. Res.* (1996) 35:635–644.

Barany et al., "Solid phase peptide synthesis" Chapter 1 in *The Peptides*, vol. 2, Academic Press, 1979, pp. 42–55.

Flörsheimer et al., "Solid–phase synthesis of peptides with the highly acid–sensitive HMPB linker" Peptides 1990: *Proceedings of the 21st European Peptide Symposium* (Giralt and Andrew, eds.), pp. 131–133.

Gordon et al., "Strategy and tactics in combinatorial organic synthesis. Applications to drug discovery" *Acc. Chem. Res.* (1996) 29(3):144–154.

Holmes et al., "Reagents for combinatorial organic synthesis: Development of a new o–nitrobenzyl photolabile linker for solid phase synthesis" *J. Org. Chem.* (1995) 60:2318–2319.

Holmes et al., "Strategies for combinatorial organic synthesis: Solution and polymer–supported synthesis of 4–thiazolidinones and 4–metathiazanones derived from amino acids" *J. Org. Chem.* (1995) 60(22):7328–7333.

Holmes et al., "Development of a new ortho–nitrobenzyl photolabile linker for solid phase synthesis" *Peptides: Chemistry, Structure and Biology*, Proceedings 14th American Peptide Symposium, Mayflower Society, 1995, pps. 44–45.

Keating et al., "Postcondensation modifications of Ugi four–component condensation products: 1–isolcyanocyclohexene as a convertible isocyanide. Mechanism of conversion, synthesis of diverse structures, and demonstration of resin capture" *J. Am. Chem. Soc.* (1996) 118:2574–2583.

Ngu et al., "Preparation of acid–labile resins with halide linkers and their utility in solid phase organic synthesis" *Tet. Lett.* (1997) 38(6):973–976.

Patel et al., "Hydroxamic acid–based bisubstrate analog inhibitors of ras farnesyl protein transferase" *J. Med. Chem.* (1996) 39(21):4197–4210.

Sharma et al., "Reductive amination with tritylamine as an ammonia equivalent: Efficient preparation of the 5–[4–[[(9–fluorenylmethyloxycarbonyl)–amino]methyl]–3, 5–dimethoxyphenoxy]valeric acid (PAL) handle for peptide synthesis" *J. Org. Chem.* (1993) 58:4993–4996.

Strocker et al., "Use of a convertible isocyanide for generation of Ugi reaction derivatives on solid support: Synthesis of α–acylaminoesters and pyrroles" *Tet. Lett.* (1996) 37(8):1149–1152.

Tempest et al., "Solid–phase, parallel syntheses by Ugi multicomponent condensation" *Angew. Chem. Int. Ed. Engl.* (1996) 35(6):640–642.

Wang, "p–Alkoxybenzyl alcohol resin and p–alkoxybenzyloxycarbonylhydrazide resin for solid phase synthesis of protected peptide fragments" *J. Am. Chem. Soc.* (1973) 95(4):1328–1333.

Wang, "Solid phase synthesis of protected peptides via photolytic cleaveage of the α–methylphenacyl ester anchoring linkage" *J. Org. Chem.* (1976) 41(20):3258–3261.

* cited by examiner

METHODS FOR SOLID-PHASE SYNTHESIS OF HYDROXYLAMINE COMPOUNDS AND DERIVATIVES AND COMBINATORIAL LIBRARIES THEREOF

CROSS REFERENCE TO RELATED APPLICATIONS

This application claims priority benefit of copending U.S. provisional patent application No. 60/047,468 filed May 23, 1997, and of copending U.S. provisional patent application No. 60/029,788, filed Oct. 28, 1996. The contents of both of these applications are hereby incorporated by reference herein in their entirety.

STATEMENT OF RIGHTS TO INVENTIONS MADE UNDER FEDERALLY SPONSORED RESEARCH

Not applicable.

TECHNICAL FIELD

This invention is directed to methods for producing combinatorial chemistry libraries containing hydroxylamines and hydroxylamine derivatives, including hydroxamic acid derivatives, hydroxylurea derivatives, and hydroxylsulfonamide derivatives. This invention is further directed to synthesis of combinatorial chemistry libraries of hydroxylamines and hydroxylamine derivatives, including hydroxamic acid derivatives, hydroxylurea derivatives, and hydroxylsulfonamide derivatives, using solid-phase techniques. This invention is still further directed to the libraries of hydroxylamines and hydroxylamine derivatives, including hydroxamic acid derivatives, hydroxylurea derivatives, and hydroxylsulfonamide derivatives, produced by the solid-phase synthetic method disclosed. This invention is still further directed to utilizing the libraries of hydroxylamines and hydroxylamine derivatives (including hydroxamic acid derivatives, hydroxylurea derivatives, and hydroxylsulfonamide derivatives) to identify and select compounds which bind to, inhibit, or otherwise affect enzymes, receptors, or other biological molecules implicated in disease processes (including disease-related metalloproteases). The hydroxylamines and hydroxylamine derivatives (including hydroxamic acid derivatives, hydroxylurea derivatives, and hydroxylsulfonamide derivatives) thus selected have potential therapeutic value.

BACKGROUND ART

The techniques of combinatorial chemistry have been increasingly exploited in the process of drug discovery. Combinatorial chemistry allows for the synthesis of a wide range of compounds with varied molecular characteristics. Combinatorial synthetic techniques enable the synthesis of hundreds to millions of distinct chemical compounds in the same amount of time required to synthesize one or a few compounds by classical synthetic methods. Subjecting these compounds to high-throughput screening allows thousands of compounds to be rapidly tested for desired activity, again saving time expense and effort in the laboratory.

Chemical combinatorial libraries are diverse collections of molecular compounds. Gordon et al. (1995) *Acc. Chem. Res.* 29:144–154. These compounds are formed using a multistep synthetic route, wherein a series of different chemical modules can be inserted at any particular step in the route. By performing the synthetic route multiple times in parallel, each possible permutation of the chemical modules can be constructed. The result is the rapid synthesis of hundreds, thousands, or even millions of different structures within a chemical class.

For several reasons, the initial work in combinatorial library construction focused on peptide synthesis. Furka et al. (1991) *Int. J. Peptide Protein Res.* 37:487–493; Houghton et al. (1985) *Proc. Natl. Acad. Sci. USA* 82:5131–5135; Geysen et al. (1984) *Proc. Natl. Acad. Sci. USA* 81:3998–4002; Fodor et al. (1991) *Science* 251:767. The rapid synthesis of discrete chemical entities is enhanced where the need to purify synthetic intermediates is minimized or eliminated; synthesis on a solid support serves this function. Construction of peptides on a solid support is well-known and well-documented. Obtaining a large number of structurally diverse molecules through combinatorial synthesis is furthered where many different chemical modules are readily available; hundreds of natural and unnatural amino acid modules are commercially available. Finally, many peptides are biologically active, making them interesting as a class to the pharmaceutical industry.

The scope of combinatorial chemistry libraries has recently been expanded beyond peptide synthesis. Polycarbamate and N-substituted glycine libraries have been synthesized in an attempt to produce libraries containing chemical entities that are, similar to peptides in structure, but possess enhanced proteolytic stability, absorption and pharmacokinetic properties. Cho et al. (1993) *Science* 261:1303–1305; and Simon et al. (1992) *Proc. Natl. Acad. Sci. USA* 89, 9367–9371. Furthermore, benzodiazepine, pyrrolidine, and diketopiperazine libraries have been synthesized, expanding combinatorial chemistry to include heterocyclic entities. Bunin et al. (1992) *J. Am. Chem. Soc.* 114:10997–10998; Murpy et al. (1995) *J. Am. Chem. Soc.* 117:7029–7030; and Gordon et al. (1995) *Biorg. Medicinal Chem. Lett.* 5:47–50.

Hydroxylamines and their derivatives, including hydroxamic acids, hydroxyl ureas, and hydroxyl sulfonamides, have been the subject of much research focused on their properties as metalloprotease inhibitors. Izquierdo-Martin et al. (1992) *J. Am. Chem. Soc.* 114:325–331; and Cushman et al. (1981) Chapter 5 "Specific Inhibitors of Zinc Metallopeptidases" in *Topics in Molecular Pharmacology* (Burgen & Roberts, eds.). Metalloproteases are believed, to be involved in the development of arthritis, tumor angiogenesis, retinopathy, and many other disease processes.

U.S. Pat. No. 5,268,384 discloses hydroxamates and hydroxyl ureas used to treat inhibit angiogenesis by inhibiting matrix metalloproteases. Among metalloproteases disclosed as targets of inhibitors are collagenases, including human skin fibroblast collagenase and purulent human sputum collagenase; gelatinases, including human skin fibroblast gelatinase and purulent human sputum gelatinase; and stromelysin. Disclosed disorders amenable to treatment by matrix metalloprotease (MMP) inhibitors include ocular pathologies such as diabetic retinopathy and neovascular glaucoma; cancer, including Kaposi's sarcoma, glioblastoma, and angiosarcoma; immune system disorders such as rheumatoid arthritis; and skin disorders such as psoriasis.

Patent publication WO 96/26918 discloses hydroxamates for inhibiting MMPs. The publication also discusses the inhibition of the production or the action of the cytokine tumor necrosis factor (TNF) by hydroxamic acid MMP inhibitors. See also, Mohler et al. *Nature* 370:218–220 (1994); Gearing et al., *Nature* 370:555–557 (1994); and McGeehan et al., *Nature* 370:558–561 (1994). These MMP inhibitors are described as useful for treating inflammatory, infectious, immunological or malignant diseases due to their effect on TNF. Among the specific diseases described are septic shock, hemodynamic shock, malaria, meningitis, fibrotic disease, cachexia, autoimmune diseases, and graft rejection.

Patent publication WO 96/25156 discloses hydroxamates for inhibiting matrix metalloproteases. The publication also discusses inhibition of production or processing of transforming growth factor alpha (TGF-α) by MMP inhibitors, and describes potential applications of the MMP inhibitors in treating inflammation; wound healing, including scar and keloid formation; diabetic retinopathy; neovascular glaucoma; atherosclerosis; vascular adhesions; systemic lupus erythrematosus; various carcinomas; and other diseases amenable to treatment by modulating production or processing of TGF-α.

U.S. Pat. No. 5,552,419 discloses aryl sulfonamido-substituted hydroxamic acids. The compounds are described as inhibitors of stromelysin, gelatinase and/or collagenase. Disorders described as amenable to treatment by the hydroxamic acid derivatives are osteoarthritis and rheumatoid arthritis; tissue ulceration; periodontal disease; bone diseases, including Paget's disease and osteoporosis; HIV infection; and tumor metastasis, tumor progression or tumor invasion.

Patent publication EP 423943 describes the use of inhibitors of certain matrix metalloproteases, such as collagenases, gelatinases, and stromelysins, as useful for treatment of demyelinating diseases such as multiple sclerosis and other scleroses; demyelinating peripheral neuropathies; acute disseminated encephalomyelitis; and other neural disorders.

Other hydroxamic acid-based metalloprotease inhibitors are described in the following patent publications: U.S. Pat. Nos. 4,599,361 and 5,256,657; European patent publications EP 236872, EP 274453, EP 489577, EP 489579, EP 497192, EP 574758; and international PCT applications WO 90/05716, WO 90/05719, WO 91/02716, WO 92/13831, WO 92/22523, WO 93/09090, WO 93/09097, WO 93/20047, WO 93/24449, WO 93/24475, WO 94/02446, WO 94/02447, WO 94/21612, WO 94/25434, and WO 94/25435.

Many synthetic routes to produce hydroxylamines have been developed and are well-known in the art (see the above-cited publications for representative examples). These methods are limited by the necessity of preparing one compound at a time. Solid-phase synthesis of an immobilized hydroxamate is mentioned in patent application WO 96/26918; however, the method used in the application is limited to the Ugi reaction described. See also, Strocker et al. *Tet. Lett.* 37:1149–1152 (1996); Keating et al., *J. Am. Chem. Soc.* 118:2574–2583 (1996); and Tempest et al. *Angew. Chem. Int. Ed. Engl.* 35:640–642 (1995), and references therein.

The invention disclosed herein provides a method for combinatorial synthesis of hydroxylamines and hydroxylamine derivatives, enabling synthesis of a much greater variety of compounds in a relatively short amount of time.

All references, publications and patents mentioned herein are hereby incorporated herein in their entirety.

DISCLOSURE OF THE INVENTION

The present invention provides a method of synthesizing a combinatorial library of hydroxylamines and hydroxylamine derivatives on a solid support, where the first step of the method is the nucleophilic addition of an alkoxyamine to an appropriate solid support. The alkyl group forming the alkoxy portion of the alkoxyamine may be a protecting group, or may be intended to remain a part of the final compounds. The solid support bound alkoxyamine is then derivatized. Following derivatization, the alkoxyamine derivatives are optionally deprotected and cleaved from the solid support.

In another embodiment, the combinatorial libraries are synthesized by adding an O-alkoxy-protected hydroxylamine-linker intermediate comprising an O-protected alkoxyamine and a linker group to a solid support bearing an amine group, derivatizing the alkoxyamine, and then optionally deprotecting the alkoxyamine derivatives and cleaving them from the solid support.

In another embodiment, the method is used to synthesize hydroxylamine and hydroxylamine derivatives selected from the group consisting of hydroxylamines, hydroxamic acids, hydroxyl ureas, and hydroxyl sulfonamides.

The invention also encompasses libraries of the compounds synthesized by the methods described. These libraries are composed of a plurality of distinct compounds where the classes of compounds include, but are not limited to, hydroxylamines and hydroxylamine derivatives, including hydroxamic acids, hydroxylureas, and hydroxylsulfonamide derivatives. The libraries preferably contain at least about 40, 50, 80, 100, 500, 1000, 5000, 10,000, 50,000, 100,000, 500,000, or 1,000,000 distinct compounds, depending on the reactions used for derivatization at each step and the degree of diversity desired in the library.

In yet another embodiment, the method is used to synthesize compounds of the formulas:

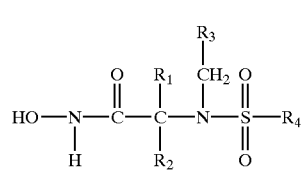

I

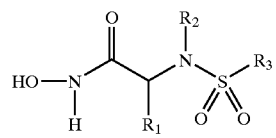

II

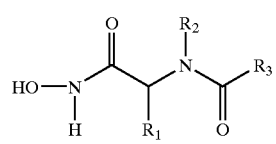

III

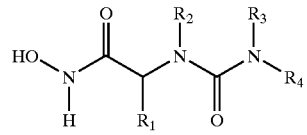

IV

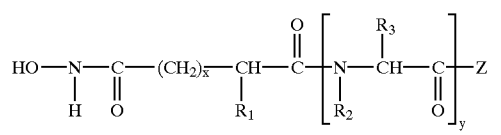

V

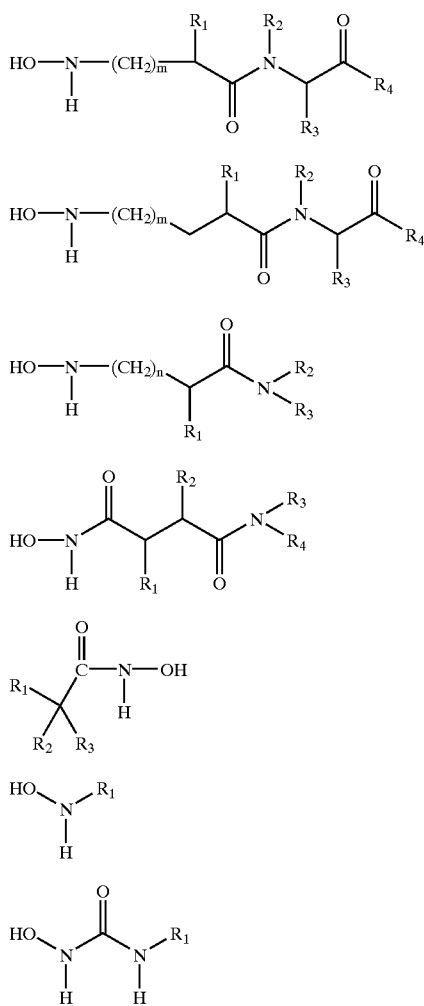

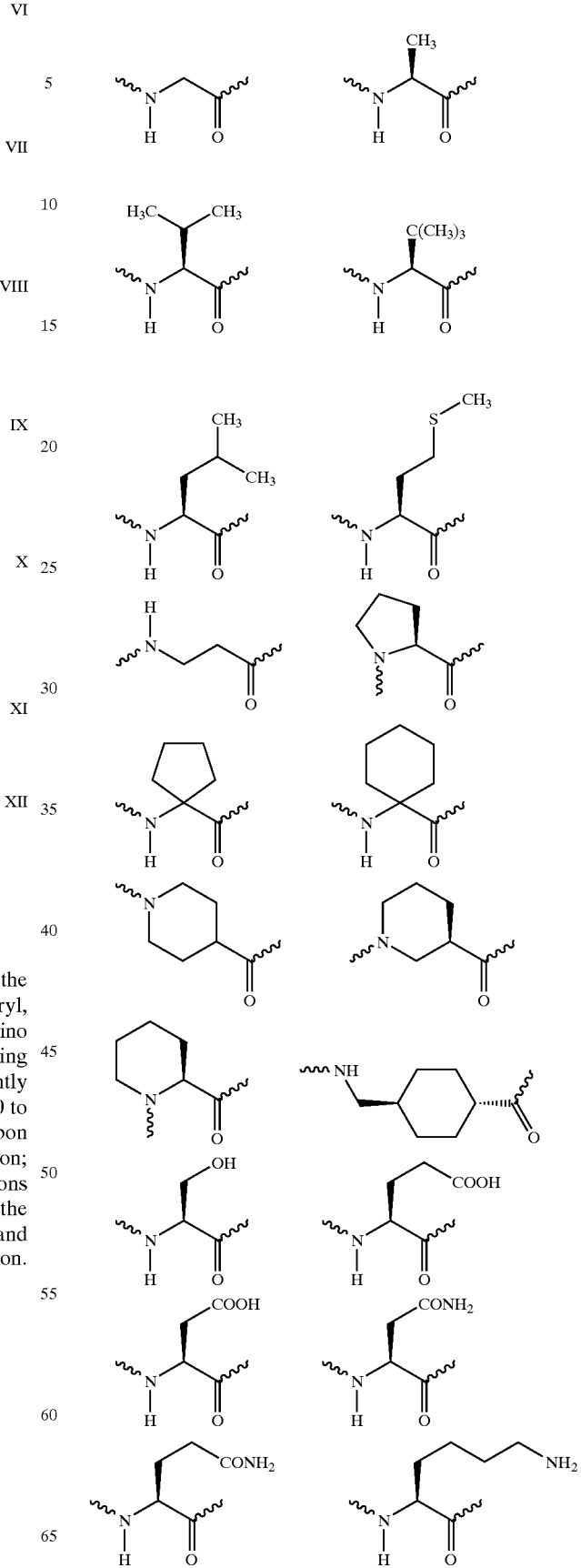

wherein the R groups are independently selected from the group consisting of H, alkyl, heteroalkyl, aryl, heteroaryl, and heterocyclic moieties as defined herein, as well as amino acid side chains (both naturally and non-naturally occurring as defined herein); m, n, and x are integers independently selected from 0 to 12; and y is an integer selected from 0 to 30. The R groups can be attached to asymmetric carbon atoms in either the R-configuration or the S-configuration; additionally, all stereoisomeric and diasteromeric variations of the compounds and substituents are included in the invention. All protected derivatives of the compounds and all salts of the compounds are also included in the invention.

These libraries include compounds of the form:

L$_3$—L$_2$—L$_1$—NHOH, where

L$_3$ is selected from the group consisting of

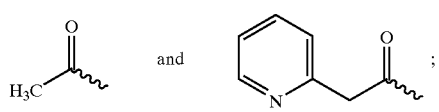

L$_2$ is selected from the group consisting of

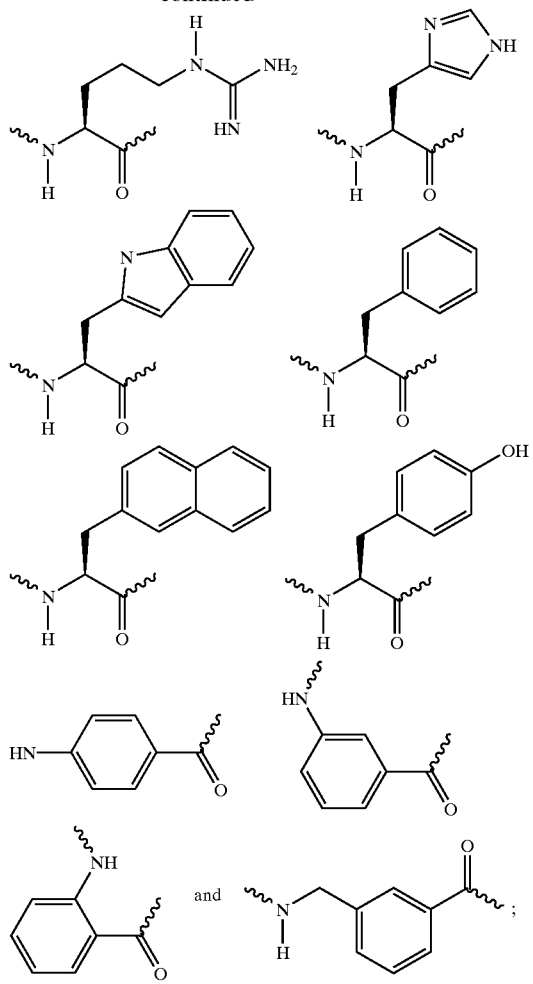
and L₁ is selected from the group consisting of
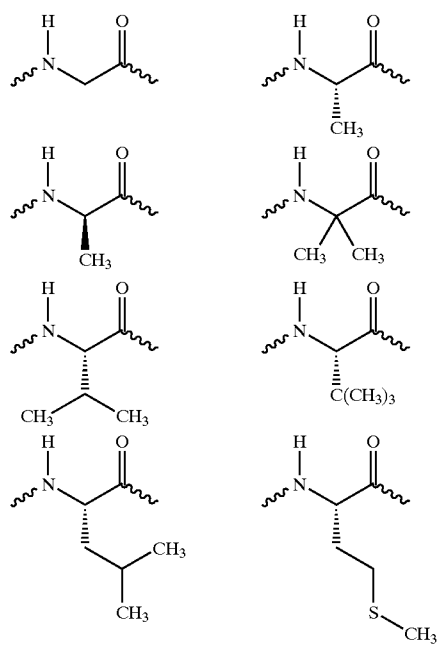
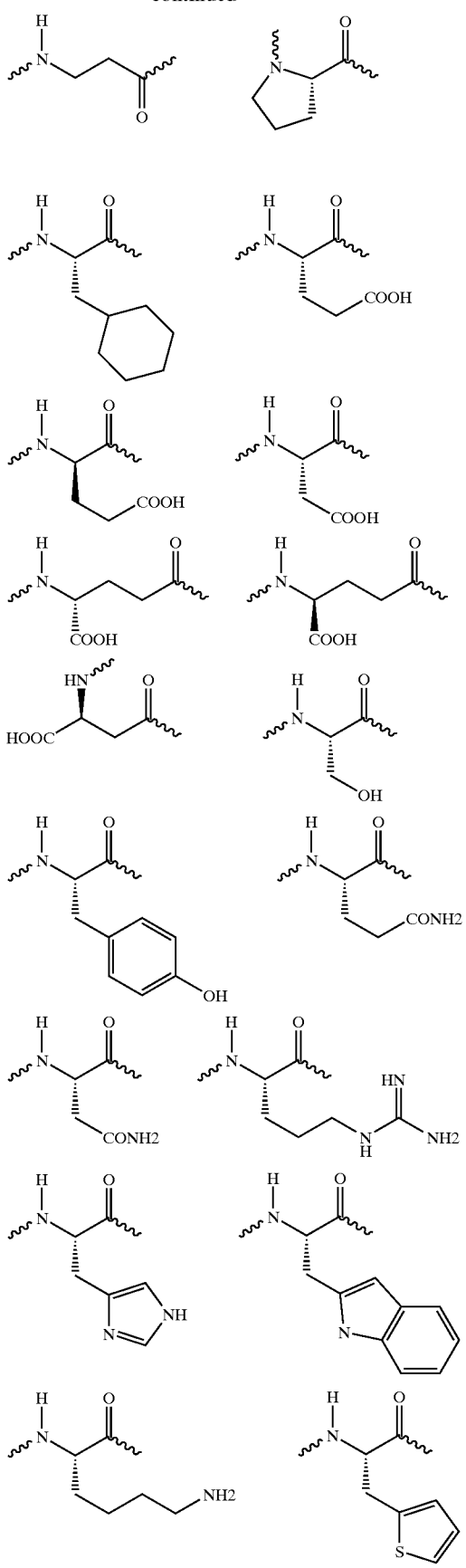

-continued
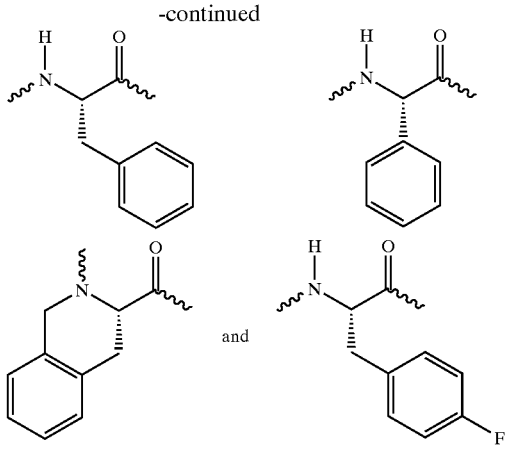
where the wavy bonds indicate the points of attachment to the rest of the molecule.
These libraries also include compounds of the form
$L_{12}-S(=O)_2-L_{11}-NHOH$,
where
$L_{12}$ is selected from the group consisting of
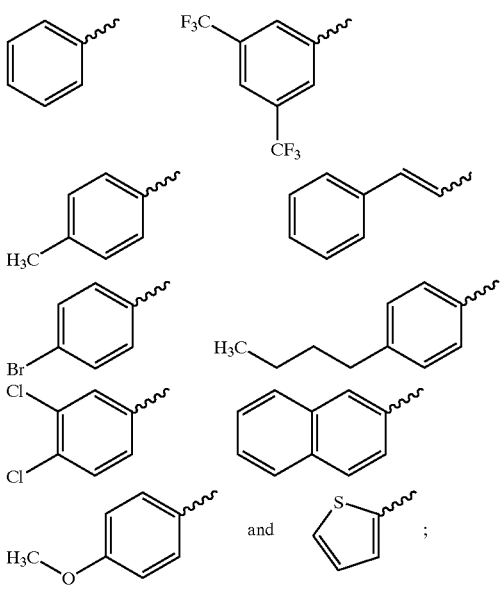
and $L_{11}$ is selected from the group consisting of
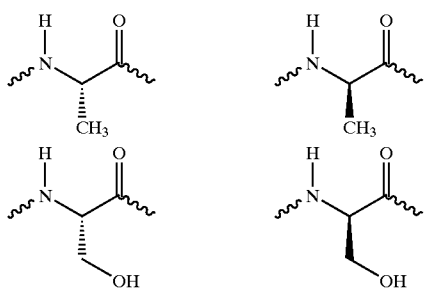
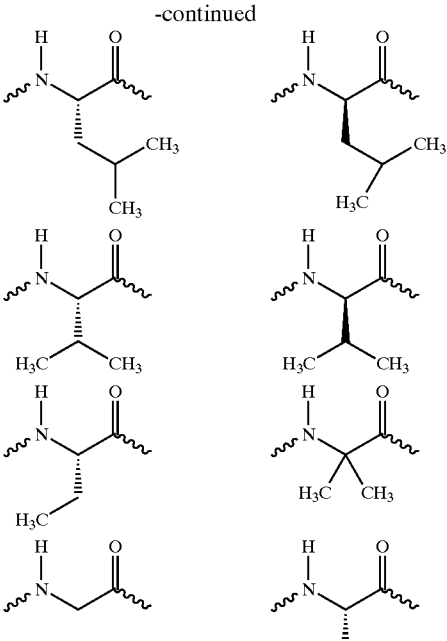
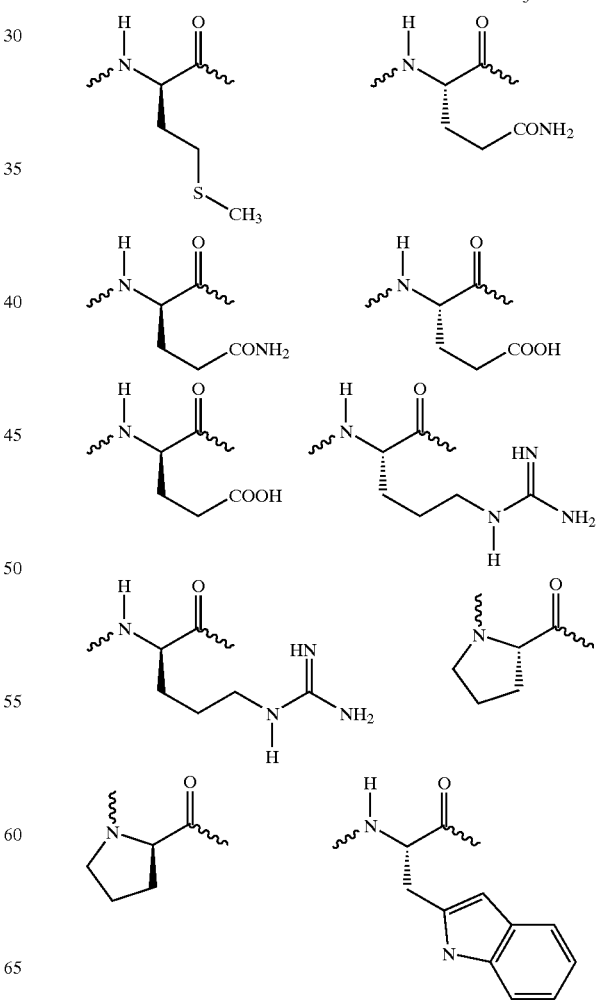

-continued
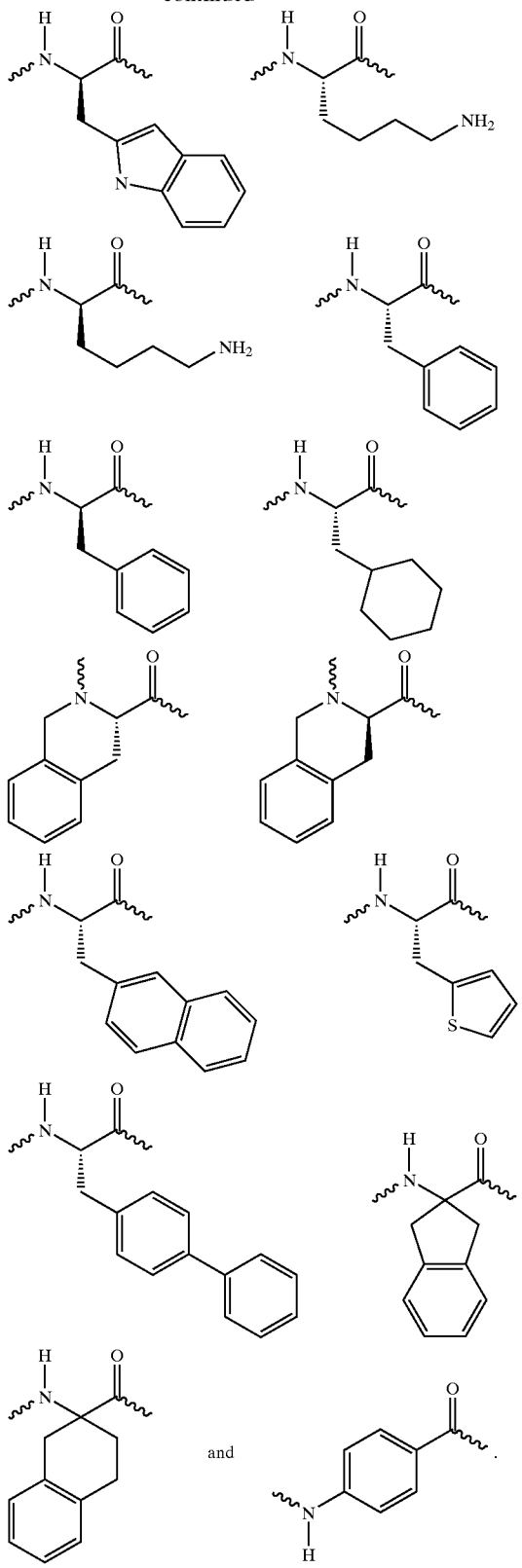
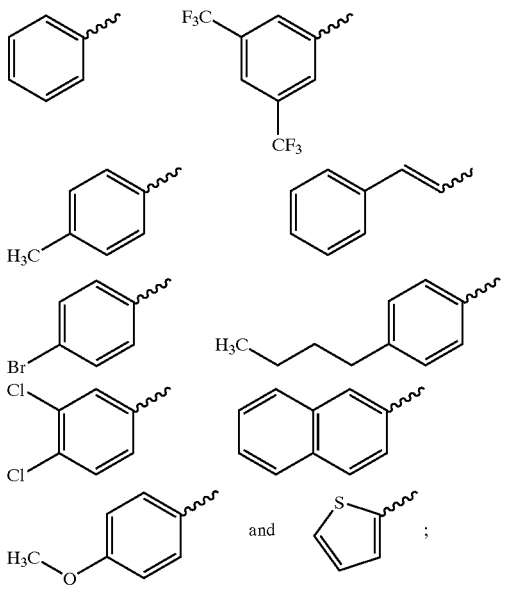
where $L_{22}$ is selected from the group consisting of
and $L_{21}$ is selected from the group consisting of
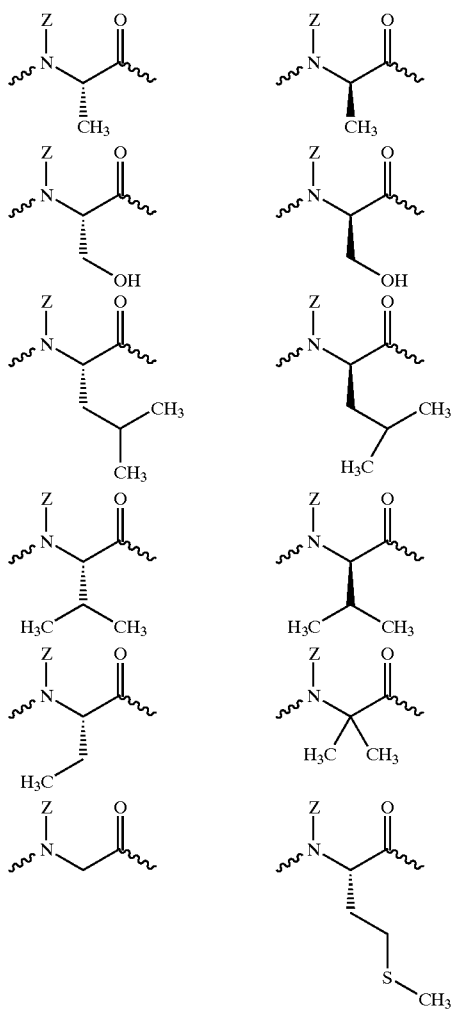
These libraries also include compounds of the form
$L_{22}$—S(=O)$_2$—$L_{21}$—NHOH

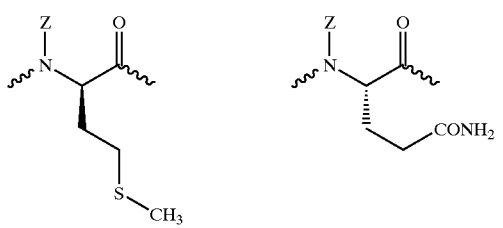
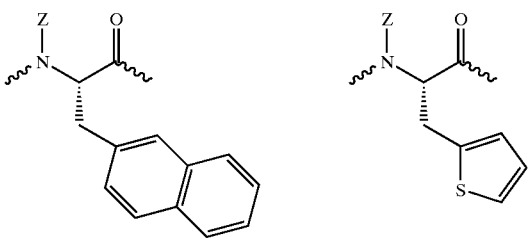
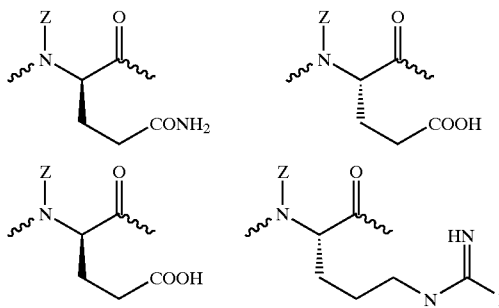
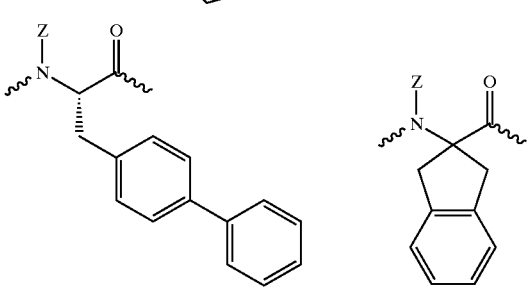
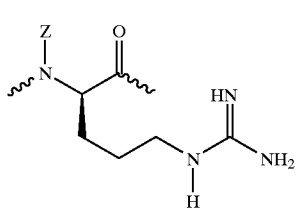
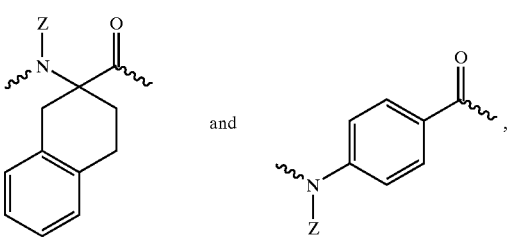
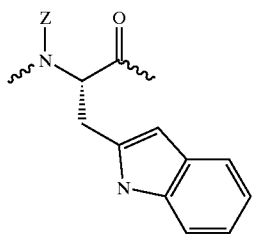
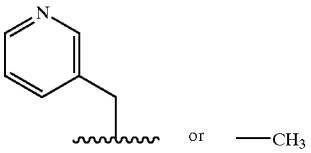
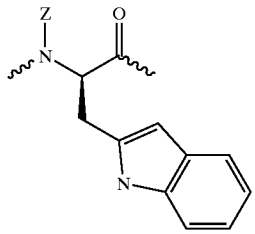
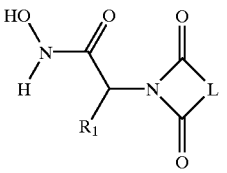 or —CH$_3$
where Z is
These libraries also include compounds of the form:
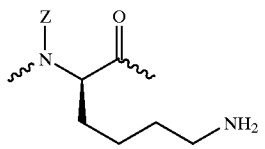
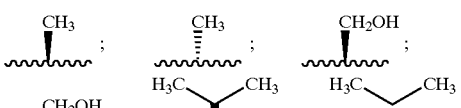
where R$_1$ is selected from the group consisting of
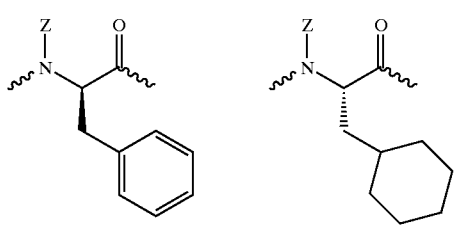
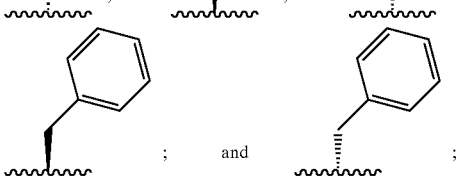

and L is selected from the group consisting of

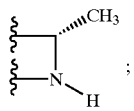 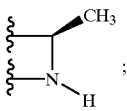

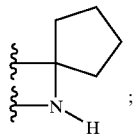 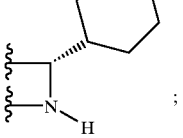

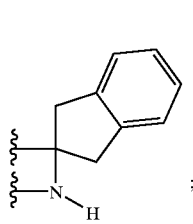 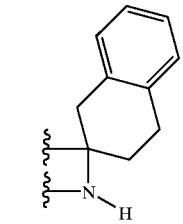

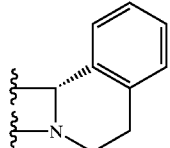 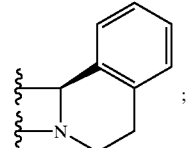

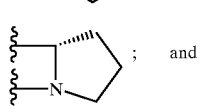 and 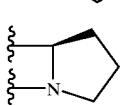

These libraries also include compounds of the form:

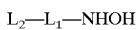

$L_2$—$L_1$—NHOH where $L_2$ is selected from the group consisting of —H, —C(=O)—CH$_3$, —C(=O)—OCH$_3$, and —C(=O)—CH$_2$—C(=O)—OH; and $L_1$ is selected from the group consisting of

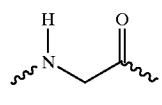 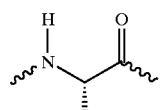

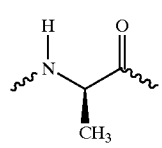 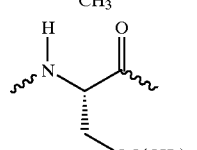

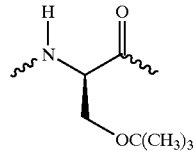 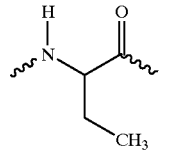

-continued

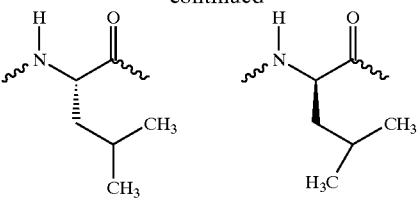

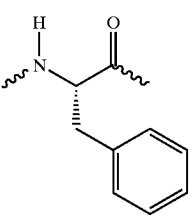 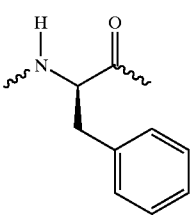

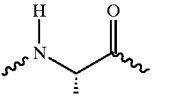

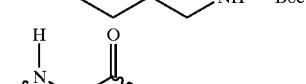

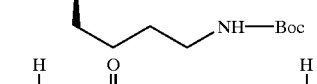

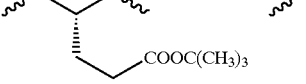

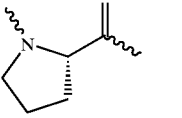 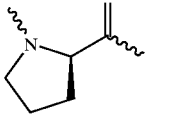

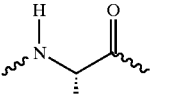 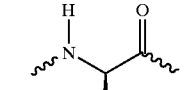

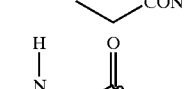 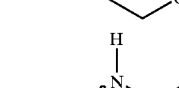

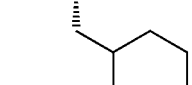 

 and 

The invention also encompasses O-protected hydroxylamine functionalized resins, prepared by displacing a leaving group on a solid support by adding an alkoxylamine nucleophile with an alkoxy protecting group, resulting in a solid support bound alkoxyamine. These alkoxylamine nucleophiles can be O-trityl hydroxylamine, O-(t-butyldimethylsilyl) hydroxylamine, O-allyl hydroxylamine, O-benzyl hydroxylamine, O-(4-methoxybenzyl) hydroxylamine, O-(2,4-dimethoxybenzyl)hydroxylamine or O-(2-tetrahydropyranyl)hydroxylamine. The leaving group can be bromide, iodide, or mesylate.

The invention also encompasses compounds of the formula

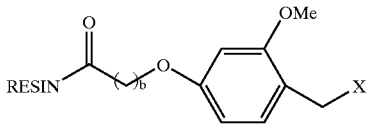

wherein b is an integer from 1 to 5, X is a leaving group selected from the group consisting of bromide, iodide, mesylate, tosylate, and p-nitrophenylsulfonate, and RESIN is any amine-bearing resin.

The invention also encompasses O-protected hydroxylamine functionalized resins, prepared by adding an O-protected hydroxylamine-linker intermediate to a solid support bearing an amine group, producing a solid support bound alkoxyamine.

The invention also encompasses an O-protected hydroxylamine-linker intermediate suitable for attachment to an amine-bearing resin. Such a compound is made up of an acid-labile linker group and an O-protected hydroxylamine.

The invention also encompasses compounds of the formula

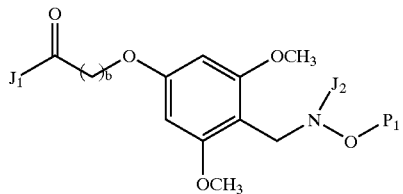

where b is an integer from 1 to 5, $P_1$ is a protecting group selected from the group consisting of 2-tetrahydropyranyl, trityl, t-butyldimethylsilyl, allyl, benzyl, 4-methoxybenzyl, and 2,4-dimethoxybenzyl protecting groups, $J_2$ is —H or -Fmoc, and $J_1$ is —OH or —NH-RESIN, where RESIN is any solid or polymeric support.

The invention also encompasses derivatized hydroxymethylphenoxy resins and derivatized 2-methoxy-4-alkoxybenzyl alcohol resins, where the active hydroxyl group of the resin is replaced with a leaving group. This leaving group can be bromide, iodide, mesylate, tosylate, or p-nitrophenylsulfonate.

The invention also encompasses compounds of the formula:

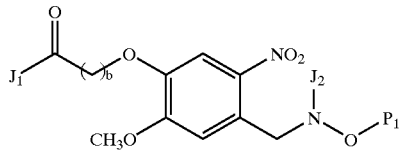

where b is an integer from 1 to 5, $P_1$ is a protecting group selected from the group consisting of 2-tetrahydropyranyl, trityl, t-butyldimethylsilyl, allyl, benzyl, 4-methoxybenzyl, and 2,4-dimethoxybenzyl protecting groups, $J_2$ is —H or -Fmoc, and $J_1$ is —OH or —NH-RESIN, where RESIN is any solid or polymeric support.

The invention also encompasses compounds of the formulas:

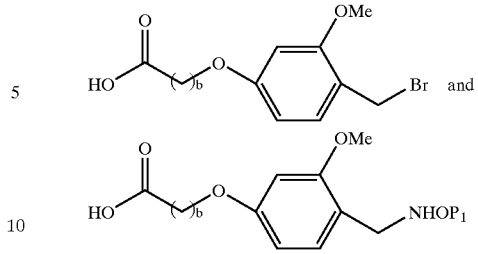

where b is an integer from 1 to 5, and $P_1$ is a protecting group selected from the group consisting of 2-tetrahydropyranyl, trityl, t-butyldimethylsilyl, allyl, benzyl, 4-methoxybenzyl, and 2,4-dimethoxybenzyl protecting groups.

The invention also encompasses methods of use of the libraries synthesized by the combinatorial methods to screen for pharmacologically active compounds.

BEST MODE FOR CARRYING OUT THE INVENTION

Figure 1:
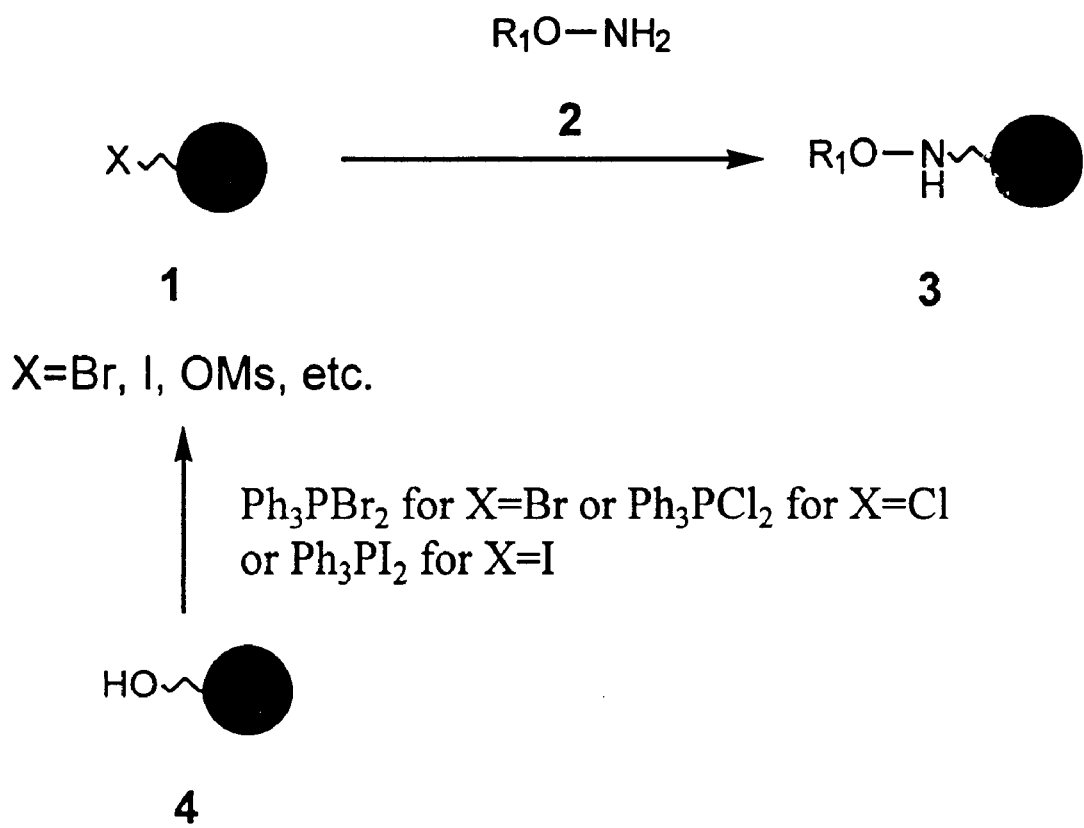
FIG. 1 illustrates a synthetic route to a resin suitable for the method of synthesis described herein.

The term "bioactive molecule," as used herein, refers to a molecule that has inhibitory activity. "Inhibitory activity" can be determined by inhibition of the interaction between a target and its respective substrate(s) or endogenous ligand(s). Target molecules include, but are not limited to, enzymes and receptors. Typically, inhibition is reduced by at least about 15% compared to the interaction of the target and substrate in the absence of the bioactive molecule, where the bioactive molecule is at a solution concentration of $10^{-3}$ molar or lower. Inhibitory activity can also be determined by exhibition of a dissociation constant of about $10^{-3}$ of the bioactive molecule with other biological macromolecules, such as DNA, RNA, polysaccharides and proteins not previously included as enzymes or receptors. Preferably, the bioactive molecule has a dissociation constant of about $10^{-4}$ molar or less. More preferably, the molecule has a dissociation constant of about $10^{-5}$ molar or less. Most preferably, the molecule has a dissociation constant of about $10^{-6}$ molar or less. These macromolecules can include, but are not limited to, macromolecules derived from prokaryotic or eukaryotic sources.

"Hydroxylamine derivatives" include any compounds which are derived from hydroxylamines, including, but not limited to, hydroxyl ureas, hydroxamic acids, and hydroxyl sulfonamides.

"Chemical library" or "array" is an intentionally created collection of differing molecules which can be prepared synthetically and screened for biological activity in a variety of different formats (e.g., libraries of soluble molecules, libraries of molecules bound to a solid support).

"Alkyl" refers to a cyclic, branched, or straight chain chemical group containing carbon and hydrogen, such as methyl, pentyl, and adamantyl. Alkyl groups can either be unsubstituted or substituted with one or more substituents, e.g., halogen, alkoxy, acyloxy, amino, hydroxyl, mercapto, carboxy, benzyloxy, phenyl, benzyl, or other functionality that can be suitably blocked, if necessary for purposes of the invention, with a protecting group. Alkyl groups can be saturated or unsaturated (e.g., containing —C=C— or —C≡C— subunits), at one or several positions. "Heteroalkyl" groups encompass alkyl chains with one or more N, O, S, or P heteroatoms incorporated into the chain, with the heteroatom bearing none, one, or more than one of the substituents described above, as well as oxidized forms of the heteroatoms N, S and P. Typically, alkyl groups will comprise 1 to 12 carbon atoms, preferably 1 to 10, and more preferably 1 to 8 carbon atoms.

"Amino acid" refers to any of the naturally occurring amino acids, as well as optical isomers (enantiomers and diastereomers), synthetic analogs and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). See, e.g., Harper et al. (1977) Review of Physiological Chemistry, 16th Ed., Lange Medical Publications, pp. 21–24. One of skill in the art will appreciate that the term "amino acid" also includes β- γ-, δ-, and ω-amino acids, and the like and α-imino acids such as proline. As used herein, "amino acids" includes proline. Non-naturally occurring amino acids are also known in the art, as set forth in, for example, Williams (ed.), *Synthesis of Optically Active α-Amino Acids,* Pergamon Press (1989); Evans et al., *J. Amer. Chem. Soc.,* 112:4011–4030 (1990); Pu et al., *J. Amer. Chem. Soc.* 56:1280–1283 (1991); and Williams et al., *J. Amer. Chem. Soc.,* 113:9276–9286 (1991); and all references cited therein.

"Aryl" or "Ar" refers to a monovalent unsaturated aromatic carbocyclic group having a single-ring (e.g., phenyl) or multiple condensed rings (e.g., naphthyl or anthryl), which are optionally unsubstituted or substituted with amino, hydroxyl, lower alkyl, alkoxy, chloro, halo, mercapto, and other substituents.

"Electron withdrawing group" refers to a substituent that draws electrons to itself more than a hydrogen atom would if it occupied the same position in a molecule. Examples of electron withdrawing groups include —NR$_2$, —COOH, —OR, —SR$_2$, —F, —COR, —Cl, —SH, —NO$_2$, —Br, —SR, —SO$_2$R, —I, —OH, —CN, —C=CR, —COOR, —Ar, —CH=CR$_2$, where R is alkyl, aryl, arylalkyl, or heteroaryl.

"Heteroaryl" or "HetAr" refers to a monovalent unsaturated aromatic carbocyclic group having a single ring (e.g., pyridyl or furyl) or multiple condensed rings (e.g., indolizinyl or benzothienyl) and having at least one hetero atom, such as N, O, or S, within the ring, optionally unsubstituted or substituted with amino, hydroxyl, alkyl, alkoxy, halo, mercapto, and other substituents.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 2nd Ed. (John Wiley & Sons, Inc., New York). Preferred terminal amino protecting groups include, but are not limited to, benzyloxycarbonyl (CBz), t-butyloxycarbonyl (Boc), t-butyldimethylsilyl (TBDIMS), 9-fluorenylmethyloxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Preferred hydroxyl protecting groups include Fmoc, TBDIMS, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxymethyloxycarbonyl).

The phrase "distinct compound" is used to refer to compounds which are chemically different, except that salts of a compound are not considered distinct from the corresponding compound from which the salt is derived. Compounds which differ in molecular formula are defined herein as distinct compounds (except for a compound and its salt). Compounds with the same molecular formula but different bond connectivities (often referred to as structural isomers), such as leucine and isoleucine, are defined herein as distinct compounds. A compound and its salt are not defined herein as distinct compounds; for example, L-valine and L-valine hydrochloride salt are not defined herein as two distinct compounds. Enantiomers and diastereomers (optical isomers) are defined herein as distinct compounds; thus, L-valine and D-valine are defined herein as two distinct compounds.

In the illustrations of libraries that can be made using the method of the invention, certain groups are drawn with wavy bonds indicating their points of attachment to the rest of the molecule. For groups written as text (e.g., —CH$_3$), the dash indicates the point of attachment to the rest of the molecule. For groups which have a bond which intersects a wavy line, the intersection point indicates the point of attachment to the rest of the molecule. Thus, for compounds of the form L$_3$—L$_2$—L$_1$—NHOH, when L$_3$, L$_2$, and L$_1$ are

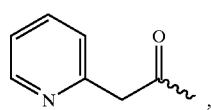,

-continued

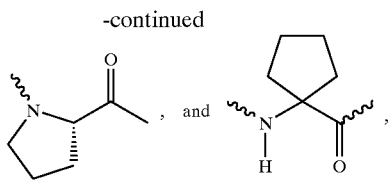

respectively, the compound

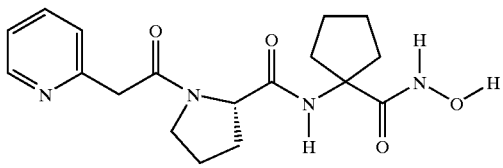

For compounds of the form $L_{12}-S(=O)_2-L_{11}-NHOH$, when $L_{12}$ and $L_{11}$ are

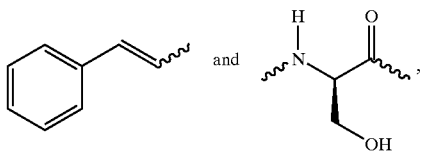

respectively, the compound is

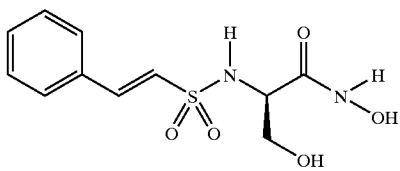

For compounds of the form $L_{12}-S(=O)_2-L_{11}-NHOH$, when $L_{12}$ and $L_{11}$ are

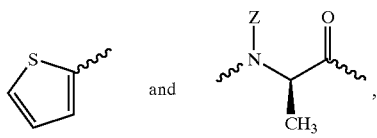

respectively, and Z is

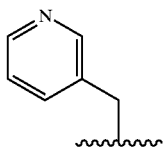

(where the Z group has a bond which intersects a wavy line), the compound is

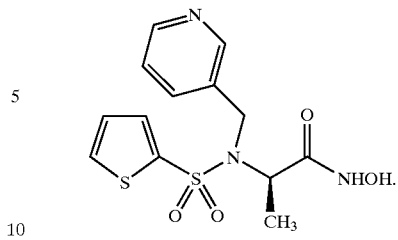

For compounds of the form

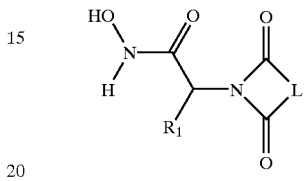

when $R_1$ is

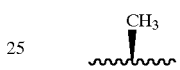

and L is

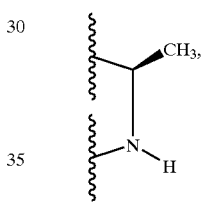

the compound is

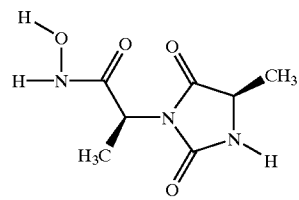

Abbreviations

The following abbreviations are used:
AcOH, HOAc=acetic acid
Ac$_2$O=acetic anhydride
BOC, Boc=t-butyloxycarbonyl
DCM=dichloromethane
DIC=diisopropylcarbodiimide
DIAD=diisopropylazodicarboxylate
DIEA=diisopropylethylamine
DMF=dimethylformamide
Et=ethyl
EtOAc=ethyl acetate
Fmoc, FMOC=9-fluorenylmethyloxycarbonyl
HATU=O-(7-aza-benzotriazol-1-yl)-N,N,N',N'-tetramethyluronium hexafluorophosphate
HBTU=O-(benzotriazol-1-yl)-N,N,N',N'-tetramethyluronium hexafluorophosphate
HHMPA=(4-hydroxymethyl-3-methoxyphenoxy)-alkanoic acid HMP resin=hydroxymethylphenoxy resin
HOAt=1-hydroxy-7-azabenzotriazole
HOBt=1-hydroxybenzotriazole
Me=methyl
Mem=methoxy ethoxy methyl ether
MeOH=methanol
MMP=matrix metalloproteinase
Mom=methoxy methyl ether
NMM=N-methyl morpholine
NPEOC=4-nitrophenethyloxycarbonyl
NPEOM=4-nitrophenethylmethyloxycarbonyl
NVOC=6-nitroveratryloxycarbonyl
NVOM=nitroveratryloxymethyl ether
PEG-PS resins or PS-PEG resin=polyethylene glycol-polystyrene graft copolymer resins
PyBOP=benzotriazole-1-yl-oxy-tris-pyrrolidino-phosphonium hexafluorophosphate
RT=room temperature
TBP=tributylphosphate
TBS, TBDIMS=t-butyldimethylsilyl
tBu=t-butyl
TES=triethylsilane
TFA=trifluoroacetic acid
TGS resin=TENTAGEL S resin
TGS $NH_2$ resin=TENTAGEL S $NH_2$ resin
THF=tetrahydrofuran
THP=2-tetrahydropyranyl
TMAD=N,N,N',N'-tetramethylazodicarboxamide (1,1'-Azobis(N,N-dimethylformamide))
TMOF=trimethylorthoformate
TPP=triphenyl phosphine
TsCl=tosyl chloride
Trt=trityl General Resins Common resins used for peptide synthesis and adaptable for combinatorial synthesis include, but are not limited to, hydroxymethylphenoxy (HMP) resin; 2-methoxy-4-alkoxybenzyl alcohol resin, and polystyrene-polyethylene glycol graft copolymer-derived resins.

Wang resin is the trade name for hydroxymethylphenoxy (HMP) resin, also called p-alkoxybenzyl alcohol resin or p-benzyloxybenzyl alcohol resin. This resin is described in Wang (1973), *J. Am. Chem. Soc.* 95: 1328. The resin has the following structure:

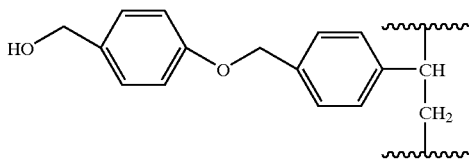

The polystyrene backbone can be crosslinked by 0.5–2.0% divinylbenzene, typically about 1% divinylbenzene.

2-methoxy-4-alkoxybenzyl alcohol resin is a resin which is highly labile to acid cleavage. It is sold under the trademark SASRIN resin (SASRIN is a registered trademark of Bachem Bioscience, King of Prussia, Pa.). This resin is described in Mergler et al., U.S. Pat. No. 4,831,084 and has the following structure:

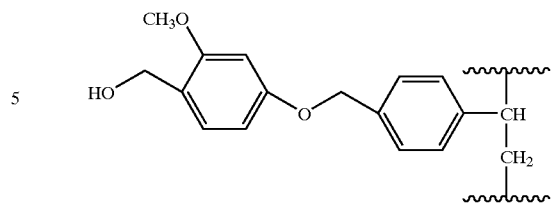

The polystyrene backbone can be crosslinked by about 0.5–2.0% divinylbenzene.

Resins comprising polyethylene glycol grafted onto polystyrene have come into wide use recently as supports for solid-phase synthesis. These resins will be generically referred to as polyethylene glycol-polystyrene graft copolymer resins, or PEG-PS resins One such PEG-PS resin is sold under the trademark TENTAGEL. Derivatives of this resin are sold under the trademark NOVASYN. TENTAGEL is a registered trademark of Rapp Polymere (Tubingen, Germany). NOVASYN is a registered trademark of Calbiochem-Novabiochem (San Diego, Calif.). The TENTAGEL polystyrene-polyethylene glycol graft copolymer resin is described in Bayer et al., U.S. Pat. No. 4,908,405. It has the following structure:

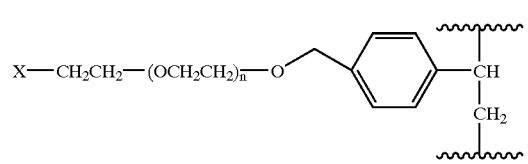

TENTAGEL

The PEG-PS resins can be generically written as

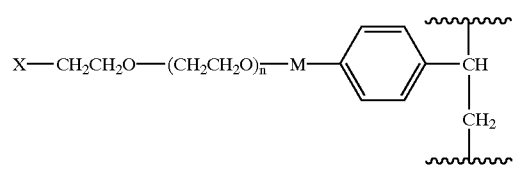

For the PEG-PS polymer TENTAGEL, M is —$CH_2$—. Other linkers M between the polyethylene glycol (PEG) polymer and the polystyrene polymer are possible; one such linker is —$CH_2CH_2$—NH—(C=O)—CH=CH—(C=O)—NH—, illustrated in Barany et al., EP 687691. The term "PEG-PS resin" or "polyethylene glycol-polystyrene graft copolymer resin" is intended to include, but not be limited to, both TENTAGEL and the polyethylene glycol-polystyrene graft copolymer resins of EP 687691. The polystyrene backbone can be crosslinked by about 0.5–10.0% divinylbenzene, preferably about 1–2% divinylbenzene. The polyethylene glycol chains can have a molecular weight of about 500 to about 40,000, corresponding to a value for n of about 10 to 1,000. A preferred range for n is about 65 to 75; a still more preferable value for n is 68. X can be selected from many functional groups, including, but not limited to, —Br, —$NH_2$, —SH, —COOH, and —OH. These resins are referred to, respectively, as bromo-terminated polyethylene glycol-polystyrene graft copolymer resin (Br-PEG-PS resin or bromo-PEG-PS resin); amino-terminated polyethylene glycol-polystyrene graft copolymer resin (amino-PEG-PS resin or $NH_2$-PEG-PS resin) (TENTAGEL S $NH_2$ resin is an example of an amino-PEG-PS resin); thiol-terminated polyethylene glycol-polystyrene graft copolymer resin (thiol-PEG-PS resin or HS-PEG-PS resin); carboxy-terminated polyethylene glycol-polystyrene graft copolymer resin (carboxy-PEG-PS resin); and hydroxy-terminated polyethylene glycol-polystyrene graft copolymer resin (hydroxy-PEG-PS resin or HO-PEG-PS resin). Resins can terminate in more elaborate groups as well, often by derivatizing the resins already described. TENTAGEL resins are commercially available from Novabiochem (San Diego, Calif.) and Peptides International (Louisville, Ky.).

Resins for Combinatorial Synthesis

A solid phase support suitable for preparing combinatorial libraries of hydroxylamine and hydroxylamine derivative compounds must anchor the synthetic intermediates stably during the chemical steps required to assemble the compounds on the support. Once synthesis of the compounds is completed, they must be capable of being cleaved from the support under conditions which do not have a significantly deleterious effect on the compounds. Solid phase supports which meet these criteria have been derived from hydroxymethylphenoxy (HMP) resin (Wang, S. S., *J. Am. Chem. Soc.* 95:1328 (1973)) (available from Advanced ChemTech, Louisville, Ky.) and TENTAGEL S AC resin (Florsheimer et al., *Peptides* 1990: Proceedings of the 21st European Peptide Symposium (Giralt and Andreu, eds.); Leiden: Escom, 1991, p. 131; available from Rapp Polymere, Tubingen, Germany, and Advanced ChemTech, Louisville, Ky.). SASRIN resin (Bachem Bioscience, King of Prussia, Pa.) can also be modified in a similar manner to HMP and TENTAGEL S AC resins and used in the method of the invention.

FIG. 1 shows various methods of preparing resins, and subsequently immobilizing a hydroxylamine derivative onto the resin. See Ngu and Patel, *Tet. Lett.* 38:973 (1997). In FIG. 1, a starting resin 4 (HMP or TENTAGEL S AC resin) is functionalized to replace the active hydroxyl group with a leaving group X, where X may be bromine, chlorine, or iodine (see Table 1 below). This functionalized resin 1 can then be reacted with a hydroxylamine of the form 2 (where $R_1$ is an alkyl group or protecting group as defined herein) to form an alkoxylamine resin 3, which can be further derivatized. Of these resins functionalized with a leaving group, bromomethylphenoxy resin (brominated HMP resin) is preferred for its high yield from parent resin (99%) and suitability for further synthetic steps. In instances where milder cleavage conditions are required, brominated or iodinated TENTAGEL S AC resin (cleavable with 5% trifluoroacetic acid) is preferred. Resins which can be used in the invention, are (but are not limited to) as follows:

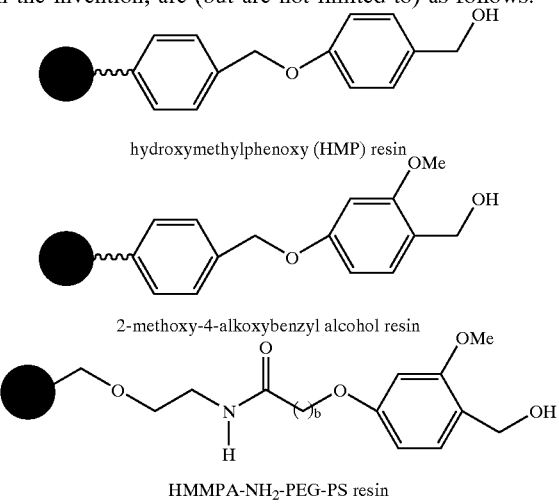

hydroxymethylphenoxy (HMP) resin 2-methoxy-4-alkoxybenzyl alcohol resin

HMMPA-NH$_2$-PEG-PS resin where HHMPA refers to the reagent

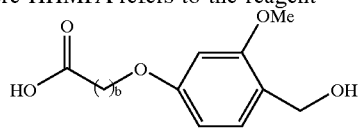

(4-hydroxymethyl-3-methoxyphenoxy)-alkanoic acid, where b is an integer from 1 to 5. An example of this type of resin is TENTAGEL S AC resin. TENTAGEL S AC resin is used in the examples below; however, any HHMPA-NH2-PEG-PS type resin can be used in an analogous fashion. Utilizing the reagents described in Table 1 gives resins of the type:

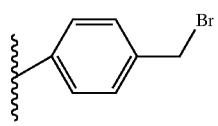

bromomethylphenoxy resin

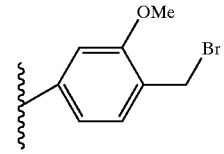

bromomethoxyalkoxybenzyl
alcohol resin or
bromo-HMMPA-NH$_2$-PEG-PS
resin (linker to remainder of
resin differs between the two resins)

Conversion of the original HMP or TENTAGEL S AC resin to the derivatized form was assayed by reacting n-butylamine with the derivatized resin, then washing away unreacted amine. The resin was then reacted with 2-naphthalenesulfonyl chloride. Resins on which the X group was displaced by nucleophilic attack of the amine yielded n-butyl-(2-naphthyl)-sulfonamide upon cleavage of the resin with trifluoroacetic acid. Resins not converted to the derivatized form, or unstable after conversion and reverted back to the original resin, yielded 2-naphthalenesulfonic acid upon cleavage. The yield of sulfonylated amine (and hence of stable derivatized resin in the scheme depicted above) is summarized in Table 1, along with the reagents used for the derivatization of the resins.

TABLE 1

Reagents for Derivatizing HMP and TENTAGEL S AC Resins

| Reagents | X (leaving group on modified resin) | Yield of Derivatived Amine from Modified HMP resin | Yield of Derivatived Amine from Modified TENTAGEL S AC resin |
| --- | --- | --- | --- |
| Ph$_3$PBr$_2$ or Ph$_3$P/CBr$_4$ | Br | 99% | 87% |
| Ph$_3$PI$_2$ or Ph$_3$P/diisopropyl azodicarboxylate/ CH$_3$I | I | 93% | 79% |
| methanesulfonyl chloride/ N-methyl morpholine | mesyl | 95% | not assayed |
| toluenesulfonyl chloride/ N-methyl morpholine | tosyl | 0% | not assayed |
| 4-nitrobenzenesulfonyl chloride/ N-methyl morpholine | nosyl | 0% | not assayed |

An alternative route to producing a resin suitable for combinatorial synthesis is provided by coupling a hydroxylamine compound to a linker in solution, then attaching the linker to an appropriate resin. The scheme below illustrates the attachment of a linker (Sharma et al., *J. Org. Chem.* 58:4993 (1993); Albericio et al., *Tet. Lett.* 32:1015 (1991); Albericio et al., *J. Org. Chem.* 55:3730 (1990) to the O-protected hydroxylamine compound $NH_2$—O—$P_1$, where $P_1$ is a protecting group. Examples of O-protected hydroxylamines include, but are not limited to, $NH_2$-O-THP (O-(2-tetrahydropyranyl) hydroxylamine), O-trityl hydroxylamine (Trt-O—$NH_2$), O-(t-butyldimethylsilyl) hydroxylamine (TBS-O—$NH_2$), O-(allyl)hydroxylamine (allyl-O—$NH_2$), O-benzyl hydroxylamine ($PhCH_2$—O—$NH_2$), O-(4-methoxybenzyl)hydroxylamine (4MeO$PhCH_2$—O—$NH_2$), O-(2,4-dimethoxybenzyl) hydroxylamine (2,4-diMeO$PhCH_2$—O—$NH_2$), and other protecting groups compatible with the chemical steps used in the synthesis. Specific examples of using the protecting groups THP and allyl are illustrated below.

Schemes for Coupling a Linking Group to the Protected Hydroxylamine

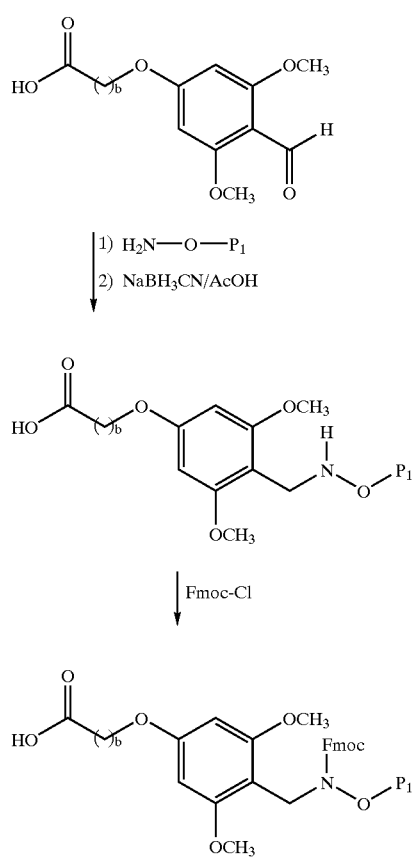

where P1 is a protecting group as described above, and b is an integer from 1 to 5.

The following scheme illustrates the synthesis of the protected hydroxylamine-linker using THP as the protecting group:

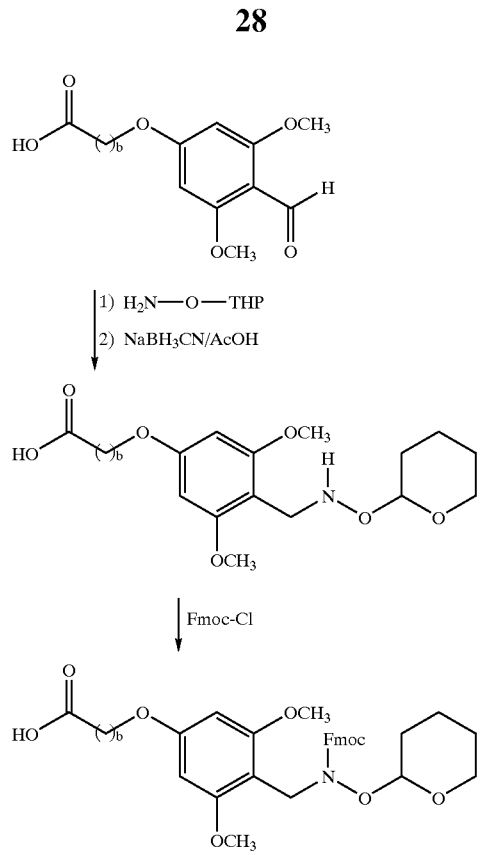

where b is an integer ranging from 1 to 5.

The following scheme illustrates the synthesis of the protected hydroxylamine-linker using allyl as the protecting group:

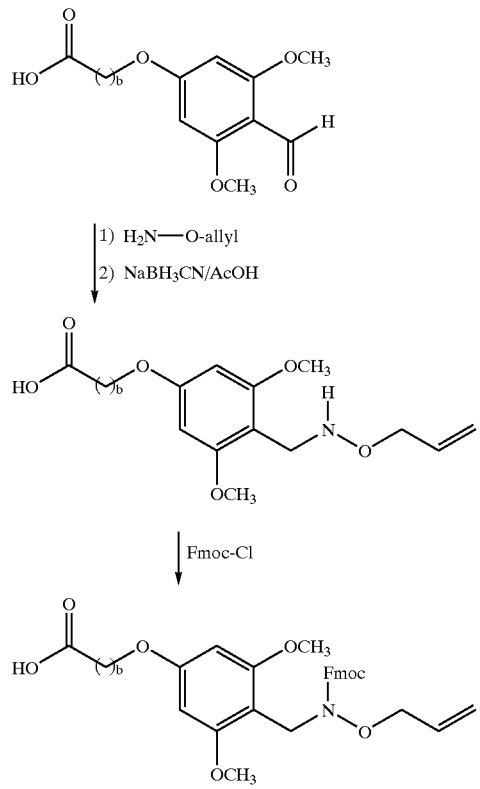

This protected hydroxylamine-linker intermediate can then be coupled to any of a variety of amine resins and then used for solid-phase combinatorial synthesis.

The following scheme depicts coupling of the protected hydroxylamine-linker to the resin, with $P_1$ a protecting group as indicated above:

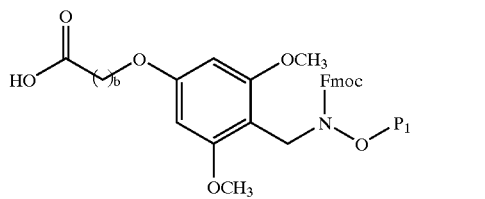

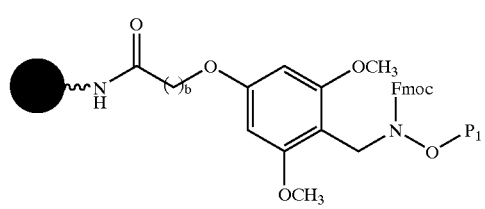

where b is an integer from 1 to 5.

The following scheme depicts coupling of the protected hydroxylamine-linker to the resin, with THP as the protecting group:

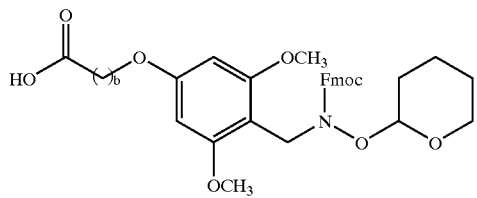

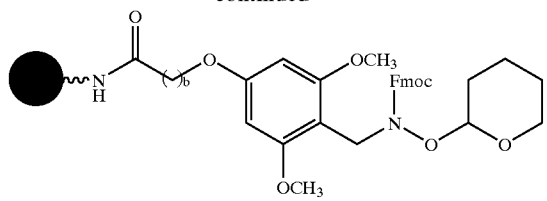

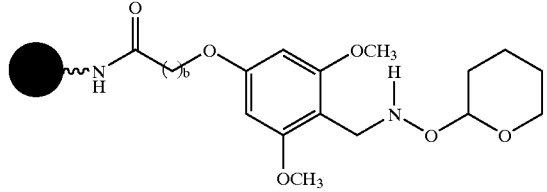

where b is an integer from 1 to 5.

The following scheme depicts coupling of the protected hydroxylamine-linker to the resin, with allyl as the protecting group:

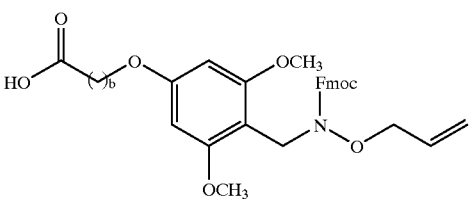

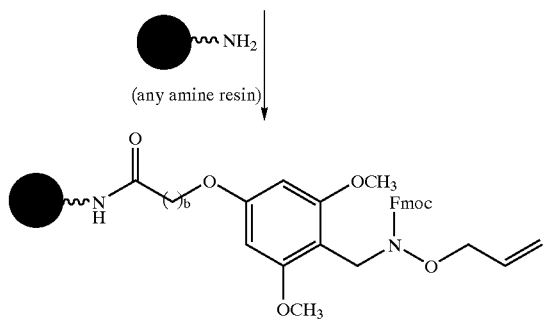

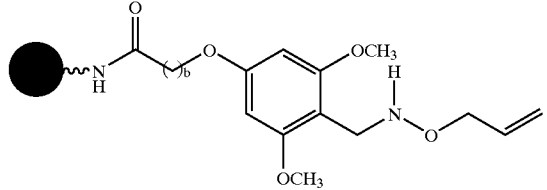

where b is an integer ranging from 1 to 5. Examples of amine resins to which the protected hydroxylamine-linker intermediate can be coupled include, but are not limited to, amino-PEG-PS resins, TENTAGEL S $NH_2$ resin, benzhydrylamine and p-methylbenzhydrylamine resins, aminomethylated polystyrene resin, and other resins bearing an amine group.

General Synthesis of Hydroxylamines and Hydroxylamine Derivatives, including Hydroxamic Acids, Hydroxylureas, and Hydroxylsulfonamides.

Figure 2:
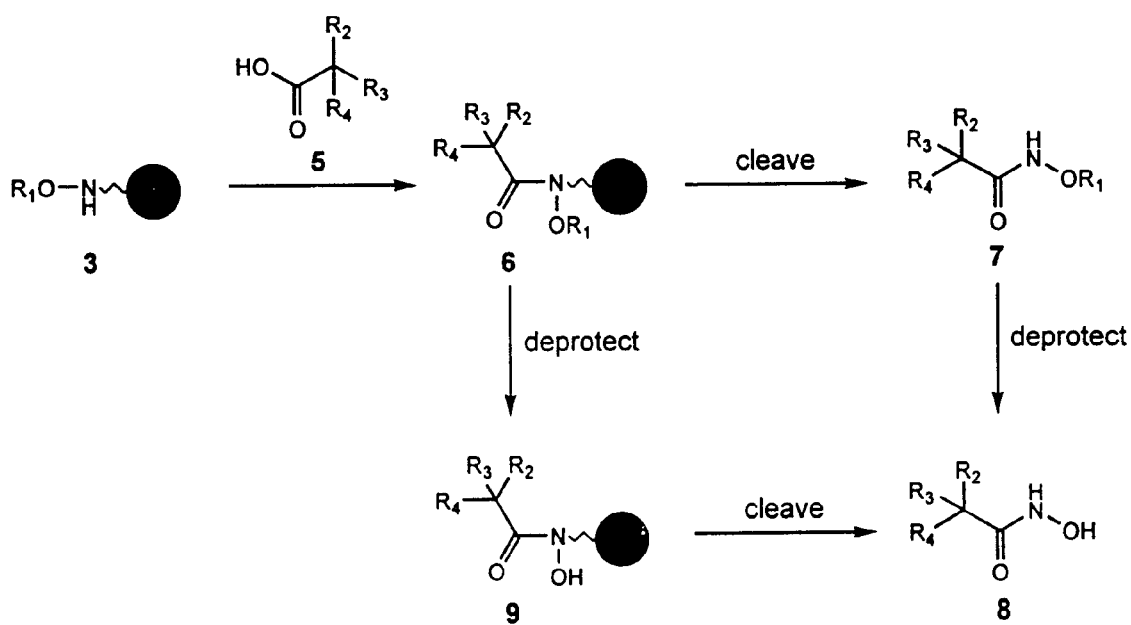
FIG. 2 illustrates a general synthetic method for synthesis of hydroxamic acid.

Hydroxylamine or hydroxylamine derivatives can be coupled to the derivatized resins for further chemical transformations, as depicted in FIG. 1. Coupling of O-protected hydroxylamines prevents side reactions from occurring at the oxygen atom of the resin-bound hydroxylamine or hydroxylamine derivative during synthesis; the O-protecting group can be removed at the end of synthesis, either before, during, or after final cleavage of the compounds from the resin. FIG. 2 illustrates the synthesis of a hydroxamic acid derivative, and also illustrates removal of the O-protecting group either before or after synthesis. In FIG. 2, the alkoxyamine resin compound 3 is reacted with a carboxylic acid 5 (where $R_2$, $R_3$ and $R_4$ are independently selected from the group consisting of H, alkyl, heteroalkyl, aryl, heteroaryl, and heterocyclic moieties as defined above, as well as naturally-occurring and non-naturally-occurring amino acid side chains) to produce a hydroxamic acid-resin compound 6. The $R_1$ group can function as an O-protecting group during the synthesis, and can be removed from the hydroxamate-resin complex to form the deprotected hydroxamate-resin complex 9; the deprotected complex is then cleaved to form the final product 8. Alternatively, the O-protected hydroxamate can be cleaved from the resin to yield the O-protected hydroxamate 7, which can then be deprotected to form the final product 8. Finally, the hydroxylamine ether 7 can be the desired product; in other words, $R_1$ functions not only as a blocking group during the synthesis, but is a desired part of the final compound, in which case it is not removed after cleavage of the hydroxamate from the resin. Representative O-protected hydroxylamine compounds include, but are not limited to, O-trityl hydroxylamine (Trt-$ONH_2$), O-(t-butyldimethylsilyl) hydroxylamine (TBS-$ONH_2$), O-(allyl)hydroxylamine (allyl-$ONH_2$), O-benzyl hydroxylamine ($PhCH_2ONH_2$), O-(4-methoxybenzyl)hydroxylamine ($4MeOPhCH_2$—O—$NH_2$), O-(2,4-dimethoxybenzyl)hydroxylamine (2,4-$diMeOPhCH_2$—O—$NH_2$), and O-(2-tetrahydropyranyl) hydroxylamine (THP-$ONH_2$ or Thp-$ONH_2$). Preferred O-protecting groups are benzyl (cleaved by hydrogenolysis) and trityl (cleaved by trifluoroacetic acid).

Figure 3:
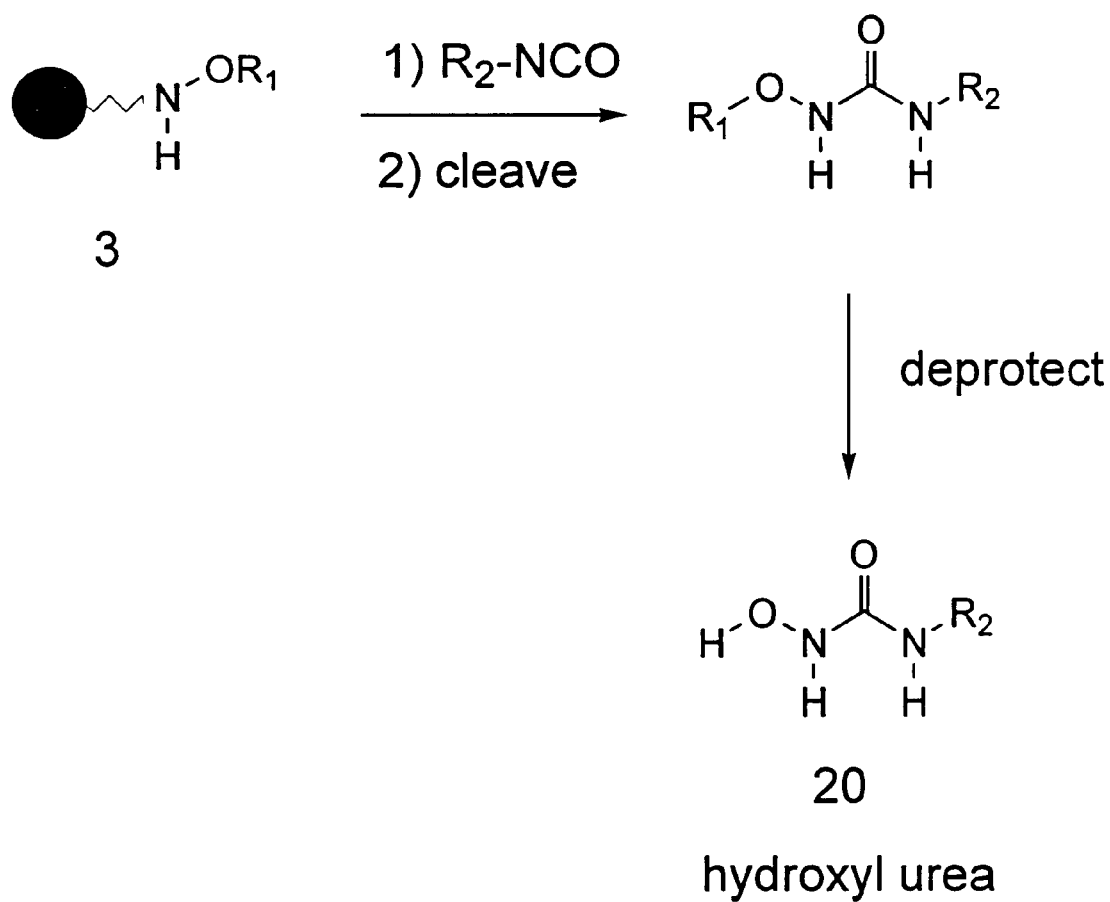
FIG. 3 illustrates a general synthetic method for synthesis of hydroxyurea.

FIG. 3 represents a general method for synthesizing hydroxylurea compounds, starting with an immobilized alkoxyamine 3 and utilizing an isocyanate compound. After synthesis is complete, cleavage and deprotection of the compound yields the hydroxyl urea 20, where $R_2$ is selected from the group consisting of H, alkyl, heteroalkyl, aryl, heteroaryl, and heterocyclic moieties as defined above, including alkyl groups substituted with naturally-occurring and non-naturally-occurring amino acid side chains.

Figure 4:
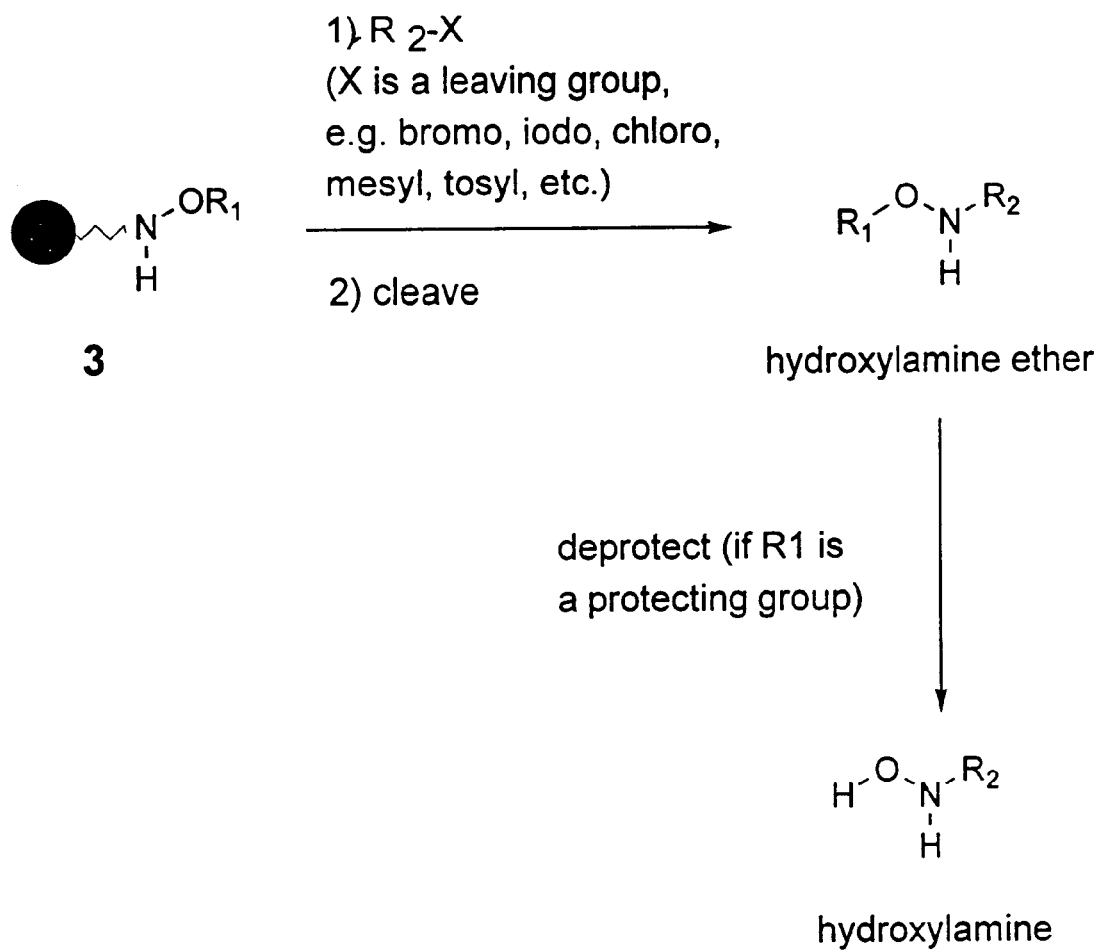
FIG. 4 illustrates a general synthetic method for synthesis of hydroxylamine or hydroxylamine ether.

FIG. 4 represents a general method for synthesizing hydroxylamines, including hydroxylamine ethers, starting with an immobilized alkoxyamine 3 and utilizing an alkylating agent. After synthesis is complete and the compound is cleaved from the resin, $R_1$ can be removed (if $R_1$ is a protecting group) to yield the hydroxylamine. Alternatively, if the hydroxylamine ether is desired (i.e., $R_1$ forms a part of the desired product), then the synthesis is complete after cleavage from the resin. $R_2$ is selected from the group consisting of H, alkyl, heteroalkyl, aryl, heteroaryl, and heterocyclic moieties as defined above, including alkyl groups substituted with naturally-occurring and non-naturally-occurring amino acid side chains.

Purification of the compounds generated in the invention can be accomplished by any of the methods of purification well-known in the art of organic synthesis, including but not limited to, recrystallization, column chromatography, flash chromatography, thin-layer chromatography, partitioning between immiscible solvents, HPLC, and affinity chromatography. Enantiomers and diastereomers can be resolved by methods well-known in the art of organic synthesis, including (but not limited to) chromatography on chiral resolving material and enzymatic resolution.

Generation of the combinatorial libraries

The general structures described above can take a wide variety of forms; substitution of various groups at any of the variable positions yields a plethora of compounds. The power of combinatorial synthesis is readily exploited by introducing a mixture of reagents at each step where a variable substituent is possible in the structure. For example, if an N-alkylated hydroxy amine is desired, the immobilized N-alkoxyamine on the resin can be reacted with a mixture of alkyl chlorides (for example butyl chloride, 2-chloropropane, and benzyl chloride). The reagents can be provided in concentrations inversely proportional to their rates of reaction with the immobilized intermediate, so that approximately equal amounts of the various components of the combinatorial mixture are produced. The reaction rates can be assayed by techniques well known in the art. One such assay involves introducing a single substituent at each of the variable steps, except at the step where coupling rates are to be assayed. At that step, an equimolar mixture of the various reagents which introduce the varied substituents can be provided. The intermediates produced after that step can be cleaved from the resin, and separated and analyzed on a GC/MS or LC/MS apparatus, or using other appropriate analytical instruments or methods. This will yield information about the relative coupling rates of the reagents used. This method is a generalization of the method for assaying reaction rates of reagents for introducing amino acids in peptide synthesis, provided by Rutter et al. in U.S. Pat. No. 5,010,175.

Instead of mixing several reagents at one step as described above, combinatorial libraries can also be prepared by using the "split and pool" protocol described by Furka et al., *Int. J. Pept. Prot. Res.* 37:487 (1991). In this method the total number of reactions grows in an additive fashion with the number of steps, but the number of compounds prepared grows in a multiplicative fashion.

Finally, a combinatorial library can also be prepared by performing parallel synthesis, where compounds are prepared in parallel as discrete compounds or as small pools of compounds.

All of these methods for generating combinatorial libraries of compounds can be performed in automated, semi-automated, or manual protocols and techniques, according to methods well known in the art.

Cleavage of compounds from the resin

Cleavage of the compounds from the derivatized HMP or TENTAGEL S AC resins is accomplished under acidic conditions. Preferably, 95–100% trifluoroacetic acid is used to cleave compounds attached to the HMP resin. A small portion (typically 5% or less) of the cleavage solution can be composed of scavenger compounds, the purpose of which is to trap carbocations released during the cleavage process to prevent the cations from reacting with the desired products. The chemical composition of the products and their sensitivity to alkylation by carbocations will determine the appropriate scavenger or scavengers. Such scavenger compounds are well-known in the field of peptide synthesis and include substances such as thiols (e.g. 1,2-ethanedithiol), phenols, trialkylsilyl compounds, anisole, thioanisole, water, and sulfides (e.g., methyl ethyl sulfide). In appropriate cases it may be desirable to reduce the amount of trifluoroacetic acid below 95% and increase the proportion of scavengers used accordingly. In cleaving compounds from TENTAGEL S AC-derived resins, typically a solution ranging from 5%–50% trifluoroacetic acid in dichloromethane is used, with the optional addition of scavengers such as those indicated above.

Use of resins incorporating photolabile linkers allows cleavage to be performed by photolysis. Photolabile resins have been described in International Patent Application WO 96/00378; in Holmes et al., (1995) *J. Org. Chem.* 60: 2318; and in Holmes et al., *Peptides: Chemistry, Structure and Biology, Proc. 14th American Peptide Symposium*, Mayflower Scientific, 1995, p. 44. Such resins are commercially available from Novabiochem (San Diego, Calif.). Particularly suitable resins are derived from hydroxymethyl-photolinker AM resin and the hydroxymethyl-photolinker NOVASYN TG resin. (The graft polymer composed of polystyrene and polyethylene glycol is sold under the trademark NOVASYN TG resin.) The hydroxymethyl group of these resins are derivatized to form bromomethyl resins by using the synthetic protocols described above under "Resins" and in Example 1 used to convert hydroxymethylphenoxy resin to bromomethylphenoxy resin. The compounds are synthesized on the support in the same fashion as for the bromomethylphenoxy resin, by displacing the bromide leaving group with an alkoxylamine nucleophile to produce a solid support bound alkoxylamine, as depicted below:

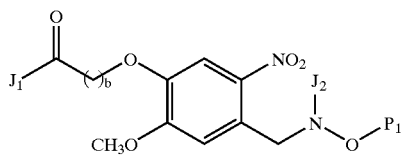

where b is an integer from 1 to 5, $P_1$ is a protecting group selected from the group consisting of 2-tetrahydropyranyl, trityl, t-butyldimethylsilyl, allyl, benzyl, 4-methoxybenzyl, and 2,4-dimethoxybenzyl protecting groups, $J_2$ is —H or -Fmoc, and $J_1$ is —OH or —NH-RESIN, where RESIN is any solid or polymeric support. Typically, RESIN is a polystyrene-type resin or a NOVASYN TG-type resin. (The graft polymer composed of polystyrene and polyethylene glycol is sold under the trademark NOVASYN TG resin.)

The compounds are derivatized in an analogous manner as in the examples. The compounds can then be cleaved from the resin using the photolysis conditions described in the references cited above. One exemplary protocol illustrated in WO 96/00378 is the suspension of 2–20 mg of resin in pH 7.4 aqueous buffer solution, followed by irradiation with a 500 W Hg ARC lamp filtered by a 350–450 nm dichroic mirror at a 10 mW/cm$^2$ power level measured at 365 nm. Irradiation time can be one hour or until satisfactory yield of cleaved compound is detected.

Screening

The present invention is directed toward the generation of libraries of hydroxylamines and hydroxylamine derivatives. These libraries are used to select one or more hydroxylamine or hydroxylamine derivative species that demonstrate a specific interaction with a targeted enzyme or receptor. An enzyme or receptor is targeted when it is believed that the enzyme or receptor is of importance in the modulation of a disease. Examples of disease states for which hydroxylamine or hydroxylamine derivative libraries can be screened include, but are not limited to, tumor growth and angiogenesis, arthritis, connective tissue disorders, inflammatory diseases, and retinopathies.

Several methods have been developed in recent years to screen libraries of compounds to identify the compounds having the desired characteristics. Typically, where a compound exhibits a dissociation constant of $10^{-6}$ or less when combined with the targeted enzyme or receptor, the compound is thought to demonstrate a specific interaction with the enzyme or receptor. Methods for isolating library compound species that demonstrate desirable affinity for a receptor or enzyme are well-known in the art.

For example, an enzyme solution can be mixed with a solution of the compounds of a particular combinatorial library under conditions favorable to enzyme-ligand binding. Binding of library compounds to the enzyme can be detected by any of the numerous enzyme inhibition assays which are well known in the art. Compounds which are bound to the enzyme can be readily separated from compounds which remain free in solution by applying the solution to a column such as a Sephadex G-25 gel filtration column. Free enzyme and enzyme-ligand complex will pass through the column quickly, while free library compounds will be retarded in their progress through the column. The mixture of enzyme-ligand complex and free enzyme can then be treated with a powerful denaturing agent, such as guanidinium hydrochloride or urea, to cause release of the ligand from the enzyme. The solution can then be injected onto an HPLC column, for example, a Vydac C-4 reverse-phase column, eluted with a gradient of water and acetonitrile ranging from 0% acetonitrile to 80% acetonitrile. Diode array detection can provide discrimination of the compounds of the combinatorial library from the enzyme. The compound peaks can then collected and subjected to mass spectrometry for identification.

An alternate manner of identifying compounds that inhibit an enzyme is to divide the library into separate sublibraries where one step in the synthesis is unique to each sublibrary. To generate a combinatorial library, reactants are mixed together during a step to generate a wide mixture of compounds. At a certain step in the synthesis, however, the resin bearing the synthetic intermediates can be divided into several portions, with each portion then undergoing a unique transformation. The resin portions are then (separately) subjected to the rest of the synthetic steps in the combinatorial synthetic method. Each individual resin portion thus constitutes a separate sublibrary. When testing the compounds, if a given sublibrary shows more activity than the other sublibraries, the unique step of that sublibrary can then be held fixed. The sublibrary then becomes the new library, with that step fixed, and forms the basis for another round of sublibrary synthesis, where a different step in the synthesis is optimized. This procedure can be executed at each step until a final compound is arrived at. The aforementioned method is the generalization of the method described in Geysen, WO 86/00991, for determining peptide "mimotopes," to the synthetic method of this invention.

While finding a compound that inhibits an enzyme is most readily performed with free compound in solution, the compounds can also be screened while still bound to the resin used for synthesis. In some applications, this may be the preferable mode of finding compounds with the desired characteristics. For example, if a compound which binds to a specific antibody is desired, the resin-bound library of compounds can be contacted with an antibody solution under conditions favoring a stable antibody-compound-resin complex. A fluorescently labeled second antibody which binds to the constant region of the first antibody can then be contacted with the antibody-compound-resin complex. This will allow identification of a specific bead as carrying the compound which is recognized by the first antibody binding site. The bead can then be physically removed from the resin mixture and subjected to mass spectral analysis. If the synthesis has been conducted in a manner such that only one compound is likely to be synthesized on a particular bead, then the binding compound has been identified. If the synthesis has been carried out so that many compounds are present on a single bead, the information derived from analysis can be utilized to narrow the synthetic choices for the next round of synthesis and identification.

The enzyme, antibody, or receptor target need not be in solution either. Antibody or enzyme can be immobilized on a column. The library of compounds can then be passed over the column, resulting in the retention of strongly binding compounds on the column after weaker-binding and non-binding compounds are washed away. The column can then be washed under conditions that dissociate protein-ligand binding, which will remove the compounds retained in the initial step. These compounds can then be analyzed, and synthesized separately in quantity for further testing. Similarly, cells expressing cell surface receptors can be contacted with a solution of library compounds. The cells bearing bound compounds can be readily separated from the solution containing non-binding compounds. The cells can then be washed with a solution which will dissociate the bound ligand from the cell surface receptor. Again, the cells can be separated from the solution, and the solution which now contains the ligands bound in the initial step can be analyzed.

Assays appropriate for measuring the inhibition or modulation of the activity of biological molecules (such as enzymes) by the compounds of the invention can be found in the following publications: Patel et al., *J. Med. Chem.* 39: 4197–4210 (1996); *Methods in Enzymology* Vol. 248, "Proteolytic Enzymes: Aspartic and Metallo Peptidases," (Alan J. Barrett, ed.), New York: Academic Press, 1995, Chapters 1–6 and 13–51; *Methods in Enzymology* Vol. 80, New York: Academic Press, 1981, Chapters 52 and 53; Cawston et al., *Biochem. J.* 195:159–165 (1981); Sellers et al., *Biochem. J.* 171:493–496 (1978); and Cawston et al., *Anal. Biochem.* 99:340–345 (1979). The patent publications mentioned in the Background Art section above also contain useful assays which can be used to determine the effects which the compounds of the invention have on biological molecules.

Pharmacological Applications

Those compounds selected as having pharmacological activity can be useful as drugs for the treatment of disease states in mammals, including humans. Such drugs comprise compounds of the invention in amounts and formulations appropriate for therapeutic effect in any of the diseases amenable to such treatment. The drugs also comprise any pharmaceutically acceptable salt of the compounds, as well as any carrier or excipient appropriate for the drug. Carriers and excipients well known in the art can be used, such as those disclosed in *Remington's Pharmaceutical Sciences*, Mack Publishing Company, Easton, Pa. The compounds of the invention, or salts thereof, can be formulated in such a manner as to be administered orally; nasally; parenterally (e.g. intravenous and intramuscularly, as a solution); in medicaments for rectal or vaginal application; in medicaments for application to the skin and mucous membranes (e.g. as solutions, lotions, emulsions, salves, plasters, etc.); and in medicaments for topical application to the eyes. The compounds can also be administered in liposome formulations. The compounds of the invention can also be administered as prodrugs, where the prodrug administered undergoes biotransformation in the treated mammal to a form which is biologically active.

The following examples are provided as illustrations of the methods described, and are not intended to limit the invention in any way.

EXAMPLES

Example 1

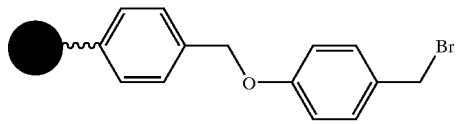

Preparation of bromomethylphenoxy resin (brominated HMP resin).

1.42 g PPh$_3$Br$_2$ (3 eq.) in 15 ml DCM was added, in 3 equal portions, to a suspension of 1 g of HMP resin (hydroxymethylphenoxy resin) (1 eq.) in 10 ml DCM at room temperature under argon. After stirring for 3 hours at room temperature, the reaction mixture was filtered, the resin was washed with DCM (4×15 ml), and dried under vacuum to give 1.066 g bromomethylphenoxy resin (99% yield).

Should a more acid-labile resin be desired, TENTAGEL S AC resin can be employed instead of HMP resin. Compounds immobilized on TENTAGEL S AC resin can be cleaved with 5% trifluoroacetic acid (TFA) solution in dichloromethane, instead of the higher concentration of TFA used below in Example 4 with the HMP resin immobilized compounds.

The corresponding iodo resins can be prepared by using PPh$_3$I$_2$ in place of PPh$_3$Br$_2$ in Example 1, above.

Example 2

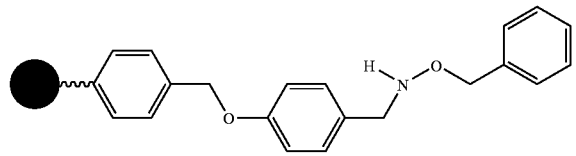

Preparation of O-benzylhydroxylamine-resin.

O-benzylhydroxylamine was prepared by partitioning 1.0 g of O-benzylhydroxylamine hydrochloride between 20 ml of ethyl acetate and 20 ml of saturated aqueous K$_2$CO$_3$ solution. The ethyl acetate layer was dried and concentrated to give O-benzylhydroxylamine. O-benzylhydroxylamine (2 ml of a 0.5 M solution in dimethylformamide (DMF)) was added to 200 mg of the bromomethylphenoxy resin of Example 1. The reaction mixture was shaken for 24 hours at room temperature. The resulting alkoxyamine resin was then washed with methanol (3×2 ml) and dichloromethane (3×2 ml).

Example 3

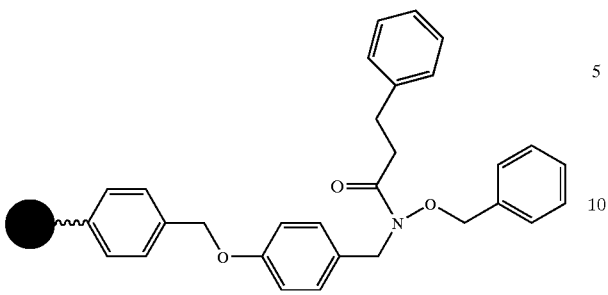

1 ml of a 0.6 M solution of 2,6-di-t-butyl-4-methylpyridine in DMF and 1 ml of a 0.5 M solution of hydrocinnamoyl chloride (3-phenylpropionyl chloride) was added to the benzylhydroxylamine resin of Example 2. The reaction was stirred at 40° C. for 18 hours. The resin was washed with methanol (3×2 ml) and dichloromethane (3×2 ml).

Example 4

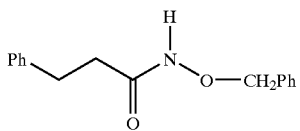

The immobilized intermediate synthesized in Example 3 was placed in a flask and 10 microliters water and 1 ml trifluoroacetic acid were added to the resin. The resin was shaken for 30 minutes. The solution was filtered and the filtrate was concentrated by evaporation and dried under vacuum to yield the compound above. $^1$H NMR (300 MHz, CDCl$_3$): 2.18 (t, 2H); 2.97 (t, 2H); 4.83 (s, 2H); 7.15 (m, 10H); 7.78 (s, 1H).

Example 5

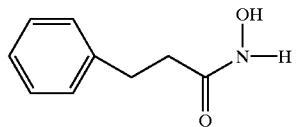

The product of Example 4 was dissolved in 10 ml of methanol. 20 mg of 10% Pd/C was added and the mixture was stirred under a hydrogen atmosphere for 5 hours at room temperature. The palladium catalyst was filtered off through a layer of Celite, and the filtrate was concentrated under vacuum to give the hydroxamic acid derivative depicted above. $^1$H NMR (300 MHz, CDCl$_3$): 2.23 (t, 2H); 2.97 (t, 2H); 7.15 (m, 5H); 7.22 (s, 1H).

Example 6

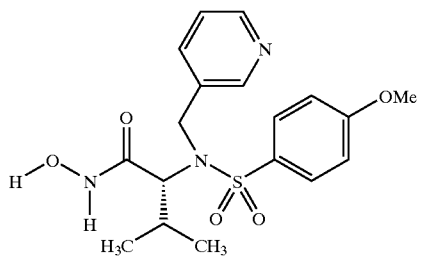

Synthesis of N-hydroxy-2(R)-[[4-methoxybenzenesulfonyl](3-picolyl)amino]-3-methylbutanamide.

The solution synthesis of the title compound is described in EP 606046. The solid-phase synthesis proceeds as follows:

Step 1. The O-benzylhydroxylamine resin product of Example 2 (1 eq.) is reacted with Fmoc-D-Valine (3 eq.), O-benzotriazole-N,N,N',N'-tetramethyluronium hexafluorophosphate (HBTU) (3 eq.), N-hydroxybenzotriazole (HOBt) (3 eq.), and N,N-diisopropylethylamine (DIEA) (4.5 eq.) in DMF for 3 hours. The reaction is repeated once with fresh reagents to ensure complete coupling. The resin is washed three times with methanol and three times with dichloromethane.

Step 2. 4-methoxybenzenesulfonyl chloride (3 eq.) and DIEA (3 eq.) are added in dichloromethane to 1 eq. of the resin from Step 1. The reaction is allowed to proceed for 3 hours, then the reagents are drained and the resin is washed six times with dichloromethane.

Step 3 can be accomplished by either of two routes:
  A. 3-(hydroxymethyl)pyridine (1 eq.), tetramethylazodicarboxamide (TMAD) (1 eq.), and triphenylphosphine (1 eq.) are added in dichloromethane to 1 eq. of the resin from Step 2. The reaction is allowed to proceed overnight. The reagents are drained and the resin is washed six times with dichloromethane.
  B. 3-(bromomethyl)pyridine (2 eq.) and diisopropylethylamine (3 eq.) are added in DMF to 1 eq. of the resin from Step 2. The reaction is allowed to proceed overnight. The reagents are drained and the resin is washed six times with dichloromethane.

Step 4. The compound is cleaved from the resin by adding 10 ml of 95% trifluoroacetic acid/5% anisole to 100 mg of the resin from Step 3. After 60 minutes, the resin is filtered on a sintered glass funnel. The filtrate is concentrated to yield the product as a trifluoroacetate salt.

Step 5. The product from step 4 is dissolved in methanol. 10% Pd/C is added and the mixture is stirred under a hydrogen atmosphere for 5 hours at room temperature. The palladium catalyst is filtered off through a layer of Celite, and the filtrate is concentrated to yield N-hydroxy-2(R)-[[4-methoxybenzenesulfonyl](3-picolyl)amino]-3-methylbutanamide.

Example 6A

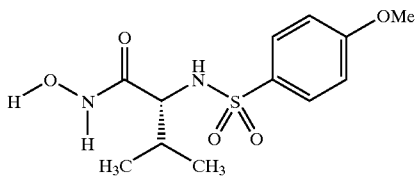

The compound depicted above is synthesized by the method of Example 6, with the exception that Step 3 is omitted.

Example 6B

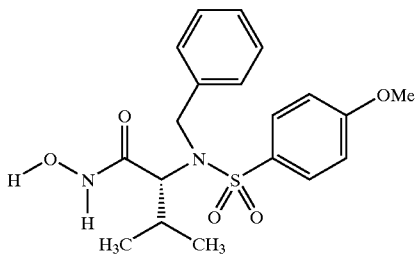

The compound depicted above is synthesized by using the method of Example 6 up to and including Step 2. Then NaN(SiCH$_3$)$_2$ and benzyl bromide are added in dimethylformamide. The reagents are drained and then Steps 4 and 5 of Example 6 are followed to yield the compound depicted.

Example 7

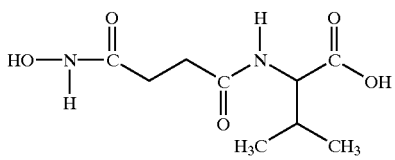

Step 1. The resin product of Example 2 (1 eq.) is reacted with succinic anhydride (4 eq.) and DIEA (4 eq.) in dichloromethane for 2 hours. The reagents are filtered from the resin and the resin is washed three times with dichloromethane.

Step 2. The resin produced in Step 1 (1 eq.) is reacted with HBTU (1 eq.), HOBt (1 eq.), and DIEA (1.0 eq.) in DMF for 1 hour. Then the benzyl ester of L-valine (3 eq.) is added in DMF to the resin suspension and allowed to react for 1 hour. The reagents are filtered from the resin and the resin is washed three times with DMF, then three times with dichloromethane.

Step 3. The compound is cleaved from the resin by adding 10 ml of 95% trifluoroacetic acid/5% anisole to 100 mg of the resin from Step 2. After 60 minutes, the resin is filtered on a sintered glass funnel. The filtrate is concentrated to yield the product as a trifluoroacetate salt.

Step 4. The product from step 3 is dissolved in methanol. 10% Pd/C is added and the mixture is stirred under a hydrogen atmosphere for 5 hours at room temperature. The palladium catalyst is filtered off through a layer of Celite, and the filtrate is concentrated to yield the compound depicted above.

Example 8

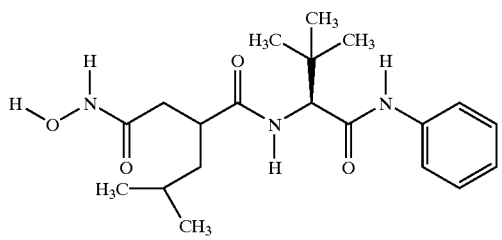

Step 1. 2-isobutyl succinic acid monomethyl ester (3 eq.), oxalyl chloride (3 eq.), and bis(trimethylsilyl)trifluoroacetamide (3 eq.) are combined in dichloromethane at 0° C. After 10 minutes the reaction mixture is added to 1 equivalent of the alkoxyamine resin product from Example 2, and the reaction is allowed to warm to room temperature. After 3 hours the reagents are drained and the resin washed six times with dichloromethane.

Step 2. A solution of 50% 1 M K$_2$CO$_3$/50% methanol is added to the resin from Step 1 and allowed to react overnight. The reagents are drained and the resin washed three times with 50% H$_2$O/50% methanol, then three times with DMF.

Step 3. A solution of diisopropylcarbodiimide (1 eq.), hydroxybenzotriazole hydrate (1 eq.), and DIEA (1 eq.) in DMF is added to the resin from Step 2 and allowed to react for 1 hour. Then the methyl ester of L-t-butylglycine (3 eq.) is added in DMF and the reaction is allowed to proceed for one hour. The reagents are removed by filtration and the resin is washed three times with DMF.

Step 4. A solution of 50% 1 M K$_2$CO$_3$/50% methanol is added to the resin from Step 3 and allowed to react overnight. The reagents are drained and the resin washed three times with 50% H$_2$O/50% methanol, then three times with DMF.

Step 5. A solution of 1-hydroxy-7-azabenzotriazole (HOAt) (3 eq.), O-(7-aza-benzotriazol-1-yl)-N,N,N',N'-tetramethyluronium hexafluorophosphate (HATU), and DIEA (4.5 eq.) is added in DMF to the resin of Step 4 and allowed to react for 1 hour. Then a solution of aniline (10 eq.) in DMF is added and the reaction allowed to proceed overnight. The reagents are drained and the resin is washed six times with DMF, then three times with dichloromethane.

Step 6. The compound is cleaved from the resin by adding 10 ml of 95% trifluoroacetic acid/5% anisole to 100 mg of the resin from Step 5. After 60 minutes, the resin is filtered on a sintered glass funnel. The filtrate is concentrated to yield the product as a trifluoroacetate salt.

Step 7. The product from step 6 is dissolved in methanol. 10% Pd/C is added and the mixture is stirred under a hydrogen atmosphere for 5 hours at room temperature. The palladium catalyst is filtered off through a layer of Celite, and the filtrate is concentrated to yield the compound depicted above.

Example 9

Generation of a combinatorial library of N-hydroxamic acids.

The procedure of Example 7 is followed, with the following modifications:

in Step 1, a mixture of succinic anhydride (1.3 eq.), maleic anhydride (1.3 eq.), and glutaric anhydride (1.3 eq.) is used in place of the succinic anhydride.

in Step 2, a mixture of the benzyl esters of all 20 naturally occurring L-amino acids is used in place of the benzyl ester of L-valine. Each amino acid benzyl ester is present in 0.15 eq.

Steps 3 and 4 are carried out as described in Example 7.

The result will be a mixture of approximately 60 distinct compounds (each compound containing one of the three anhydride groups and one of the 20 amino acids). If desired, an equimolar mixture of the compounds can be prepared by measuring the kinetics of coupling of the various components and adjusting the ratios in solution to ensure equal amounts of coupling. The coupling rates of the various anhydrides can be measured by 1) preparing the pure intermediate product of Step 1 for each anhydride; 2) determining the elution of each pure intermediate using an analytical method such as HPLC; 3) reacting a mixture of anhydrides as described in this example, Step 1; 4) determining the ratios of the products of Step 1 produced; and 5) adjusting the concentrations of the anhydrides so that they are present in concentrations which are inversely proportional to their rate of coupling. The coupling of the various amino acids can be determined in a similar manner, except that acid hydrolysis of the product of Step 4 of this example and amino acid analysis is used to determine the relative amounts of amino acid coupled. Note that tryptophan cannot be quantitated by acid hydrolysis, and asparagine and glutamine will be converted to aspartate and glutamate, respectively. The concentrations of these amino acids in the pool of compounds can be assayed by other methods of amino acid analysis well-known in the art.

Example 10

Synthesis of Protected Hydroxylamine-Linker-Resin:

Compound 53:

O-tetrahydropyranylhydroxylamine (Compound 51) (1.3 g) and Compound 52 (2.6 g, 0.9 equiv.; purchased from PerSeptive Biosystems) in THF (30 ml) and trimethyl orthoformate (TMOF) (5 ml) were stirred for 2 hr at room temperature under nitrogen. Acetic acid (HOAc) (35 μl) and 1 M NaCNBH$_3$ in THF (19.4 ml, 2 equiv.) were added to the mixture and stirred for 18 hr. Solvent was removed under reduced pressure. The crude material was loaded on a silica gel column and eluted with DCM-MeOH-HOAc (99-0.15-0.04). Yield: 2.58 g, 63%. $^1$H NMR (300 MHz, CDCl$_3$) δ1.24–1.77 (m, 6H), 2.04–2.13 (m, 2H), 2.52–2.57 (t, J=7.14, 2H), 3.53 (m, 2H), 3.77 (s, 6H), 3.97–4.01 (t, J=6.17, 3H), 4.14 (d, J=2.2, 2H), 4.89 (t, J=2.47, 1H), 6.08 (s, 2H).

Compound 54

To Compound 53 (1.0 g) and DIEA (0.948 ml, 2 equiv.) in DCM (20 ml) was added Fmoc-Cl (0.73g, 1.05 equiv.). The reacture mixture was stirred for 2 hr at room temperature under argon. Solvent was removed under vacuum and the crude oil was redissolved in EtOAc (50 ml) and washed with 0.5 N aqueous HCl (1×50 ml), then H$_2$O (1×50 ml). The organic layer was dried with MgSO$_4$, filtered and solvent removed under vacuum. The crude oil was loaded on a silica gel column and eluted with DCM-MeOH-HOAc (99-0.08-0.02). Yield: 1.42 g, 89%.

Compound 55

Compound 54 (780 mg, 1.1 equiv.), HATU (502 mg, 1.1 equiv.) and DIEA (694 μl, 3.3 equiv.) were added to TENTAGEL S NH$_2$ resin (5 g, 0.24 mmole/g) in DMF (5 ml); the reaction mixture was then shaken for 5 hr. The resin was filtered and washed with MeOH (3×8 ml) and THF (3×8 ml). The resin was dried under vacuum to give compound 55.

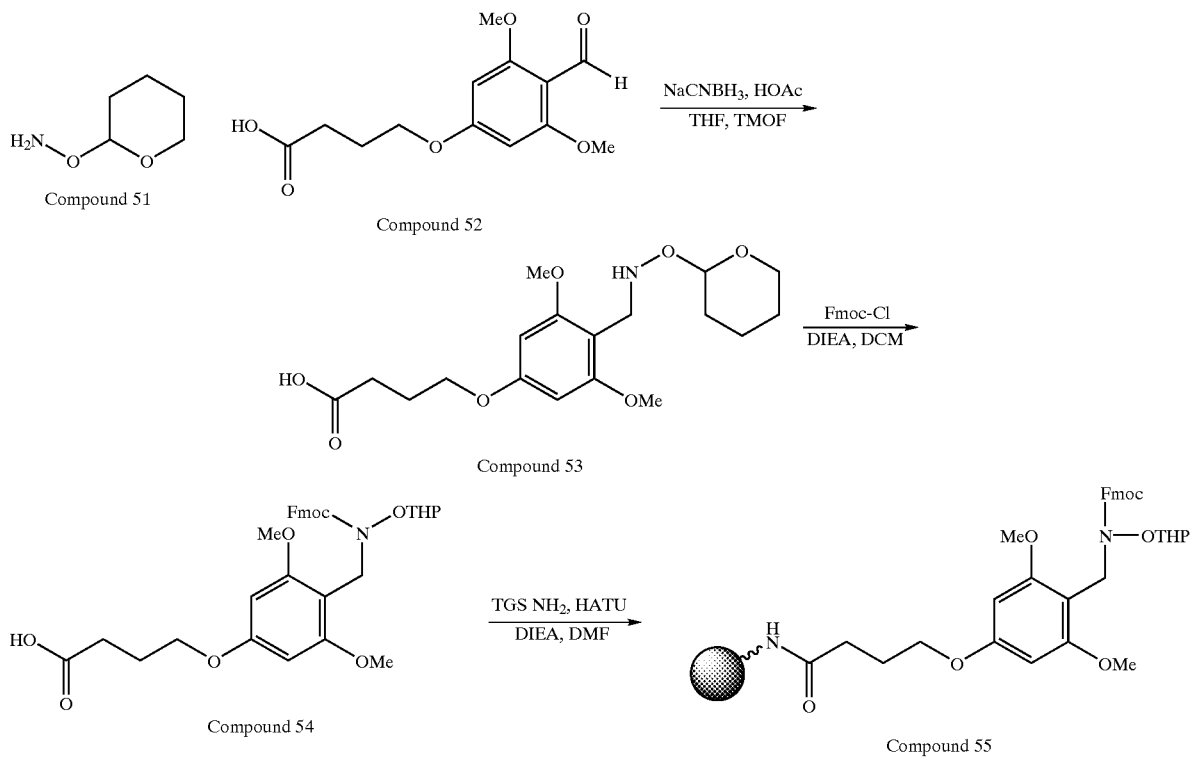

Example 11

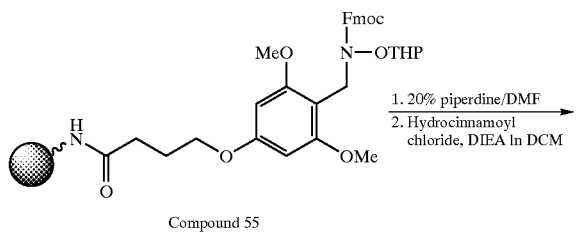

Derivatization of Resin-Bound Protected Hydroxylamine:

Preparation of Compound 56

Compound 55 from Example 10 (300 mg) was treated with 20% piperidine/DMF (5 ml) for 20 min. The resin was washed with MeOH (3×5 ml) and DCM (2×5 ml). DIEA (126 μl, 10 equiv.) and hydrocinnamoyl chloride (53.4 μl, 5 equiv) in DCM (5 ml) were added at room temperature under nitrogen. The reaction mixture was shaken for 18 hr. The resin was then washed with MeOH (3×5 ml) and DCM (2×5 ml).

2.5% TFA, 1% $H_2O$ in DCM (4 ml) was added to the resin, and the reaction mixture shaken for 1 hr, followed by washes with MeOH (3×5 ml) and DCM (2×5ml).

5% $H_2O$, 50% TFA in DCM was then added to the resin and shaken for 1 hr. The resin was filtered; the filtrate was removed and the solvent evaporated to give compound 56. $^1$H NMR (300 MHz, CDCl$_3$) δ2.23 (t, 2H), 2.97 (t, 2H), 7.15 (m, 5H).

Example 12

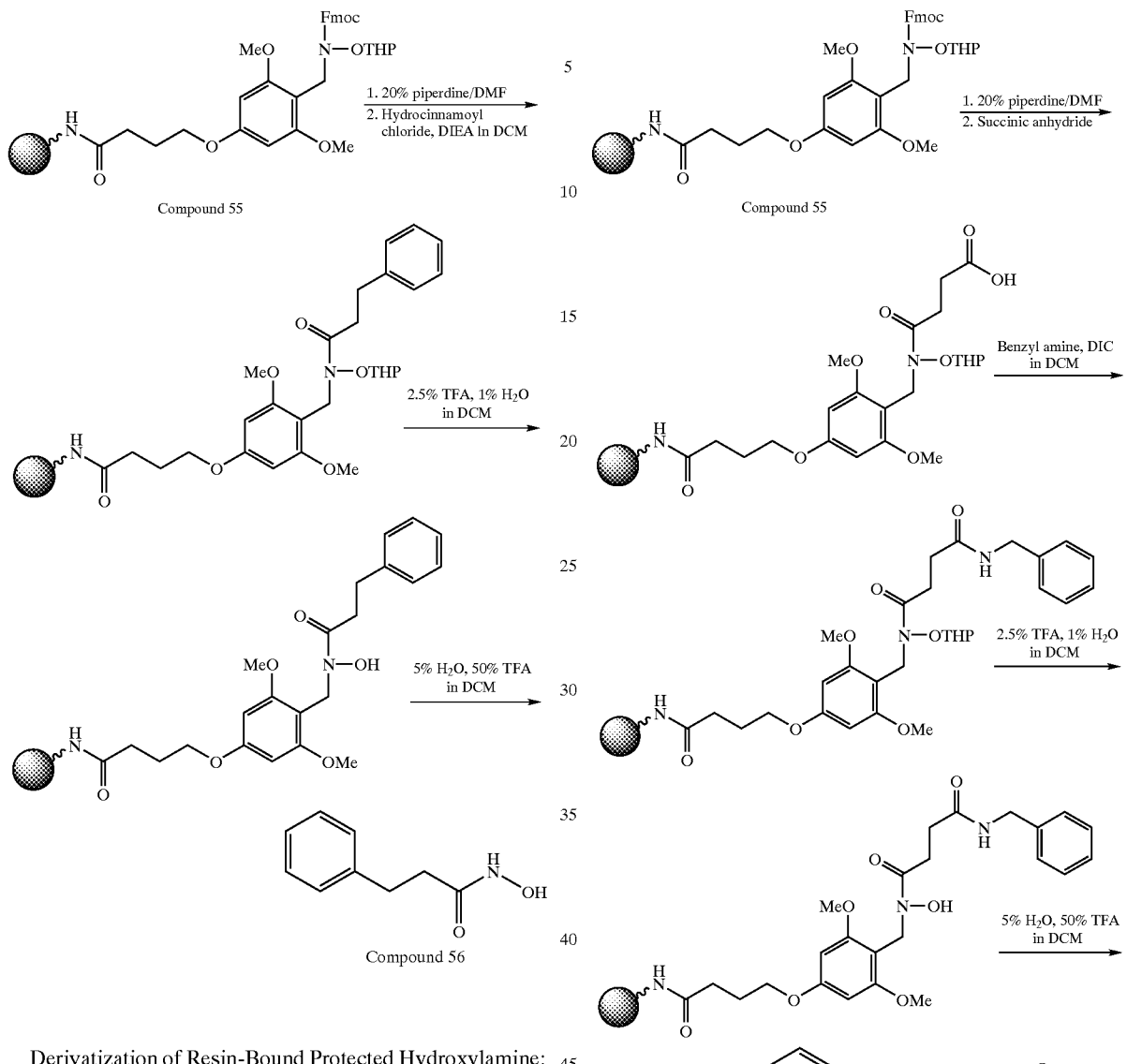

Derivatization of Resin-Bound Protected Hydroxylamine.

Preparation of Compound 57

Compound 55 from Example 10 (300 mg) was treated with 20% piperidine/DMF (5 ml) for 20 min. The resin was washed with MeOH (3×5 ml) and DCM (2×5 ml). 1 M succinic anhydride in DMF (5 ml) was added to the resin at room temperature under nitrogen, and the reaction mixture shaken for 18 hr. The resin was washed with MeOH (3×5 ml) and DCM (2×5 ml).

Benzyl amine (78.6 μl, 10 equiv.) and DIC (113 μl, 10 equiv.) were added to the resin in DCM (5 ml). The reaction mixture was shaken for 18 hr at room temperature under nitrogen. The resin was washed with MeOH (3×5 ml) and DCM (2×5 ml).

2.5% TFA, 1% H$_2$O in DCM (4 ml) was added to the resin, and the reaction mixture shaken for 1 hr, followed by washes with MeOH (3×5ml) and DCM (2×5 ml).

5% H$_2$O, 50% TFA in DCM was added to the resin and shaken for 1 hr. The resin was filtered; the filtrate was removed and evaporated to give compound 57. $^1$H NMR (300 MHz, CDCl$_3$) δ3.66 (m, 2H), 4.44 (d, 2H), 7.27 (m, 5H).

Example 13

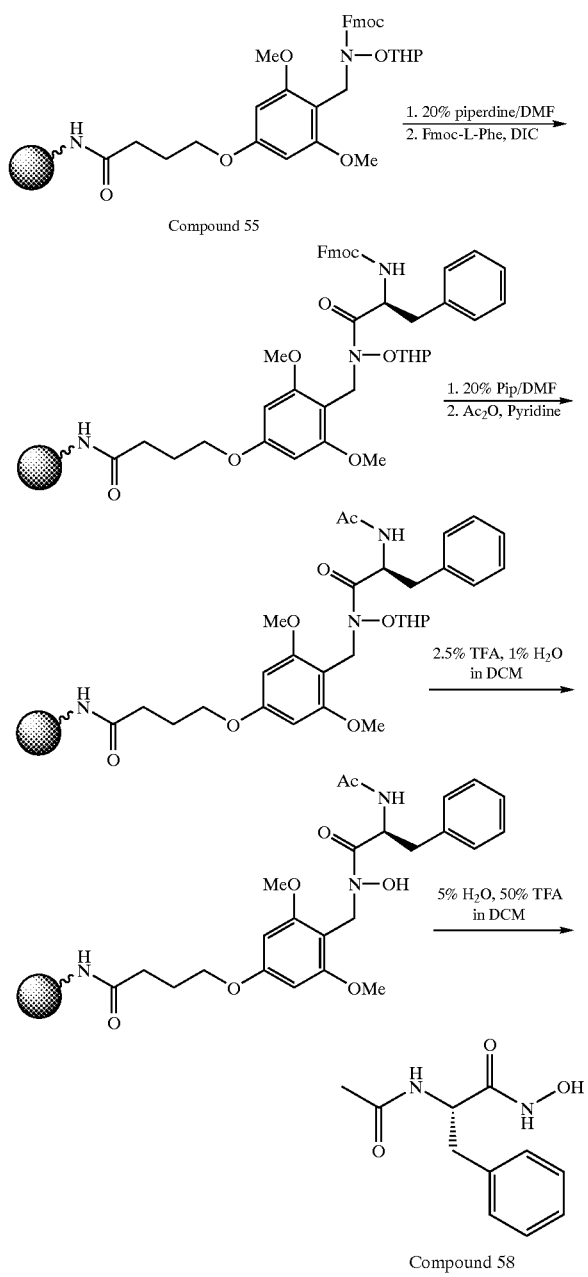

Derivatization of Resin-Bound Protected Hydroxylamine: Preparation of Compound 58

Compound 55 from Example 10 (300 mg) was treated with 20% piperidine/DMF (5 ml) for 20 min. The resin was washed with MeOH (3×5 ml) and DCM (2×5 ml). Fmoc-L-Phe (280 mg, 10 equiv.) and DIC (56 μl, 5 equiv.) were added to the resin in DMF (5 ml) at room temperature under nitrogen. The reaction mixture was shaken for 18 hr. The resin was washed with MeOH (3×5ml) and DCM (2×5ml).

20% Piperidine/DMF (5 ml) was added to the resin and the reaction mixture shaken for 20 min. The resin was washed with MeOH (3×5 ml) and DCM (2×5 ml).

Pyridine (2 ml) and acetic anhydride (1 ml) were added to the resin and shaken for 2 hr. The resin was washed with MeOH (3×5 ml) and DCM (2×5 ml).

2.5% TFA, 1% H$_2$O in DCM (4 ml) was added to the resin, and the reaction mixture shaken for 1 hr and washed with MeOH (3×5 ml) and DCM (2×5 ml).

5% H$_2$O, 50% TFA in DCM was added to the resin and shaken for 1 hr. The resin was filtered; the filtrate was removed and evaporated to give compound 58. $^1$H NMR (300 MHz, CDCl$_3$) δ1.91 (s, 3H), 3.03 (m, 2H), 4.59 (m, 1H), 7.27 (m, 5H).

Example 14

Figure 5:
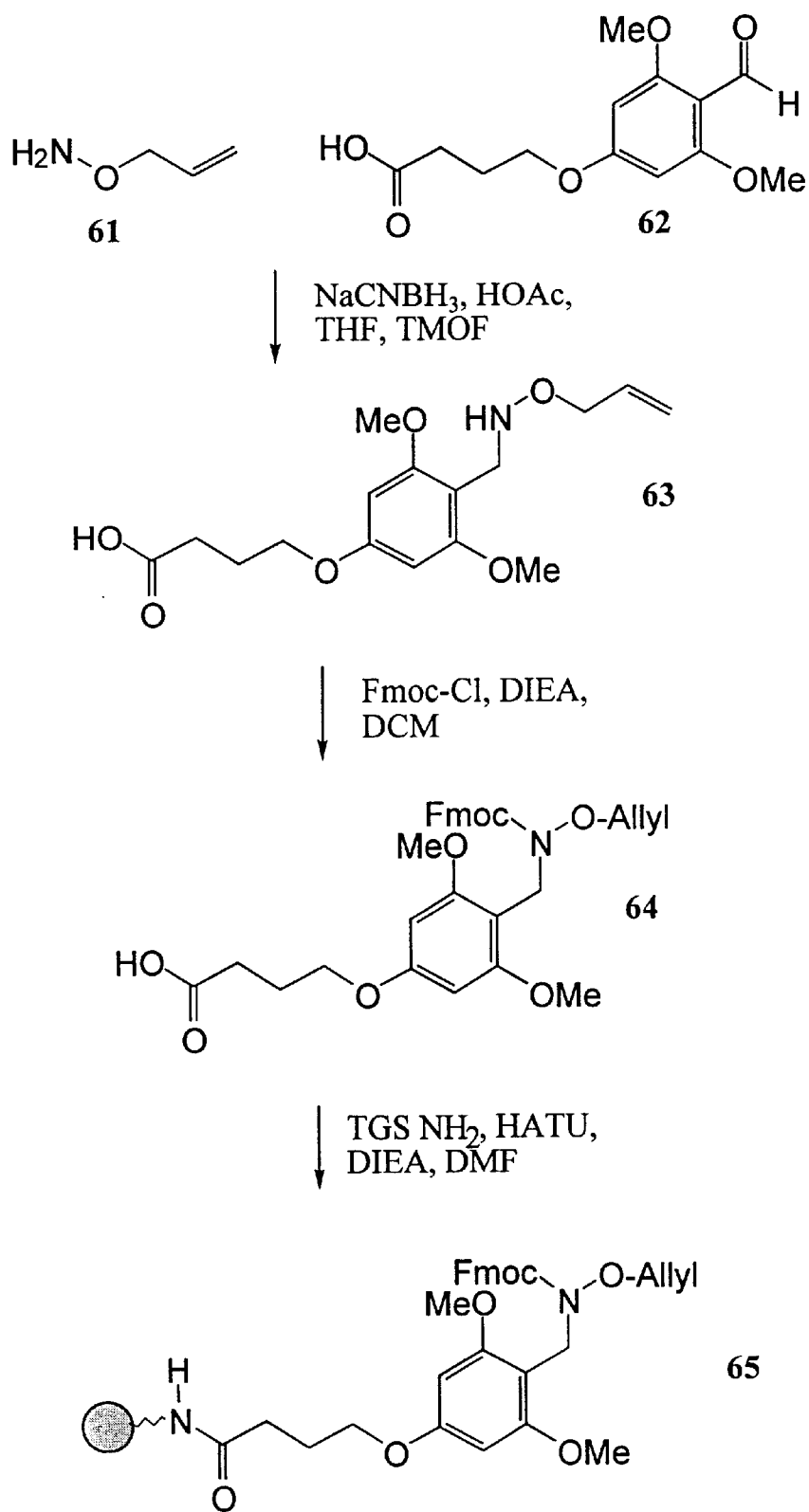
FIG. 5 illustrates a synthetic route to an O-allyl protected hydroxylamine resin.

Synthesis of Compound 63 (see FIG. 5)

O-allylhydroxyamine (Compound 61) (637 mg) and Compound 62 (2.6 g, 0.9 equiv.) in THF (30 ml) and trimethyl orthoformate (TMOF) (5 ml) were stirred for 2 hr at room temperature under nitrogen. Acetic acid (35 μl) and 1 M NaCNBH$_3$ in THF (19.4 ml, 2 equiv.) were added to the mixture and stirred for 18 hr. Solvent was removed under reduced pressure. The crude material was loaded on a silica gel column and eluted with DCM-MeOH-AcOH (99-0.15-0.04). Yield: 2.2 g, 70%. $^1$H NMR: (300 MHz, CDCl$_3$) δ2.03–2.10 (m, 1H), 2.21–2.26 (m, 1H), 2.45–2.50 (t, J=7.55 Hz, 2H), 3.77 (s, 3H), 3.81 (s, 3H), 3.96–4.00 (t, J=6.32 Hz, 1H), 4.10–4.14 (t, J=5.22 Hz, 1H), 4.40 (s, 2H), 4.55–4.60 (dd, J=6.32 Hz, J=4.26 Hz, 2H), 5.39–5.45 (m, 2H), 5.76–5.90 (m, 1H), 6.05–6.11 (m, 2H).

Example 15

Synthesis of Compound 64 (see FIG. 5)

To Compound 63 (1.0 g) and DIEA (1.07 ml, 2 equiv.) in DCM (20 ml) was added Fmoc-Cl (0.835 g, 1.05 equiv.), and the reaction mixture was stirred for 2 hr at room temperature under argon. Solvent was removed under vacuum and the crude oil was redissolved in EtOAc (50 ml) and washed with 0.5 N aqueous HCl (1×50 ml) and H$_2$O (1×50 ml). The organic layer was dried with MgSO$_4$, filtered and the solvent removed under vacuum. The crude oil was loaded on a silica gel column and eluted with DCM-MeOH-HOAc (99-0.08-0.02). Yield: 1.51 g, 89%. $^1$H NMR: (300 MHz, CDCl$_3$) δ2.034–2.099 (m, 1H), 2.09–2.15 (m, 2H), 2.55–2.62 (m, 2H), 3.76–3.81 (t, J=6.87 Hz, 6H), 3.96–4.13 (m, 3H), 4.26–4.31 (m, 1H), 4.46–4.51 (t, J=7.28 Hz, 2H), 4.79 (d, J=3.85 Hz, 2H), 5.06–5.16 (m, 2H), 5.62–5.79 (m, 1H), 6.09 (m, 2H), 7.26–7.41 (m, 4H), 7.65–7.76 (m, 4H).

Example 16

Synthesis of Compound 65 (see FIG. 5)

Compound 64 (655 mg, 1.1 equiv.), HATU (502 mg, 1.1 equiv.) and DIEA (694 μl, 3.3 equiv.) were added to TENTA-GEL S NH$_2$ resin (5 g, 0.24 mmole/g) in DMF (5 ml), and the reaction mixture shaken for 5 hr. The resin was filtered and washed with MeOH (3×8 ml) and THF (3×8 ml). The resin was dried under vacuum to give Compound 65.

Example 17

Figure 6:
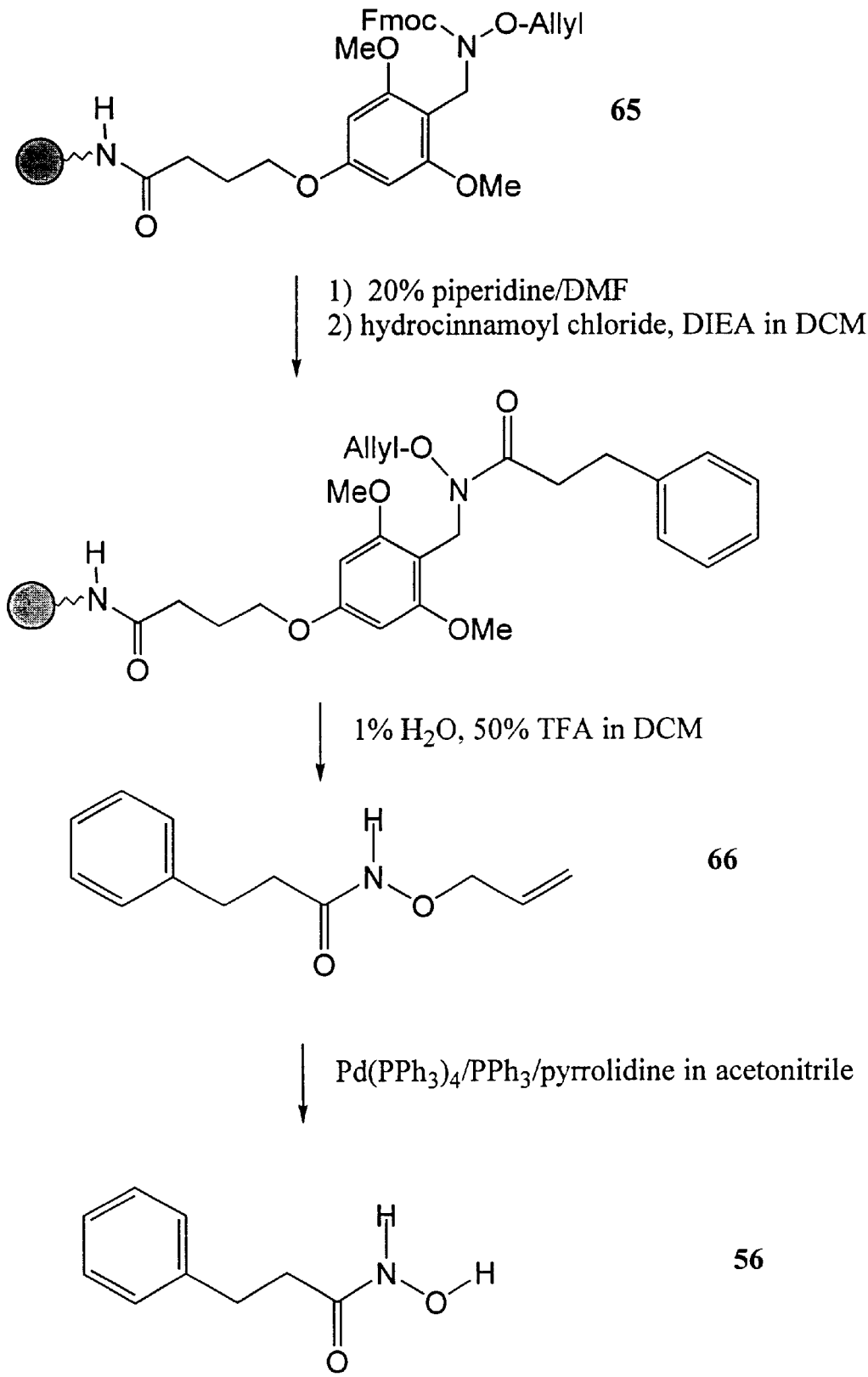
FIG. 6 illustrates a synthetic route to an O-allyl protected hydroxylamine compound.

Synthesis of Compound 56 (see FIG. 6)

20% piperidine in DMF (5 ml) was added to Compound 65 (300 mg) and the resin shaken for 20 minutes. The resin was washed with MeOH (3×5 ml) and DCM (2×5 ml). DIEA (126 µl, 10 equiv.) and hydrocinnamoyl chloride (53.4 µl, 5 equiv.) in DCM (5 ml) were added at room temperature under nitrogen. The reaction mixture was shaken for 18 hr. The resin was washed with MeOH (3×5 ml) and DCM (2×5 ml). Then 1% $H_2O$, 50% TFA in DCM was added to the resin and the resin shaken for 1 hr. The resin was filtered and the solvent was removed from the filtrate to yield Compound 66. $^1$H NMR: (300 MHz, $CDCl_3$) δ2.19 (br-s, 2H), 2.97 (t, 2H), 4.36 (br-s, 2H), 5.27 (m, 2H), 5.83 (m, 1H),7.18(m, 5H).

To Compound 66 (100 mg) in acetonitrile (2 ml) was added tetrakis(triphenylphosphine)palladium(0) (11.6 mg), triphenylphosphine (5.3 mg), and pyrrolidine (50 µl) at room temperature under argon. The reaction was stirred for 18 hr., the solvent was removed under reduced pressure, and the crude material was purified by preparatory TLC (5% MeOH in DCM). $^1$H NMR: (300 MHz, $CDCl_3$) δ2.23 (t, 2H), 2.97 (t, 2H), 7.15 (m, 5H).

Example 18

Figure 7:
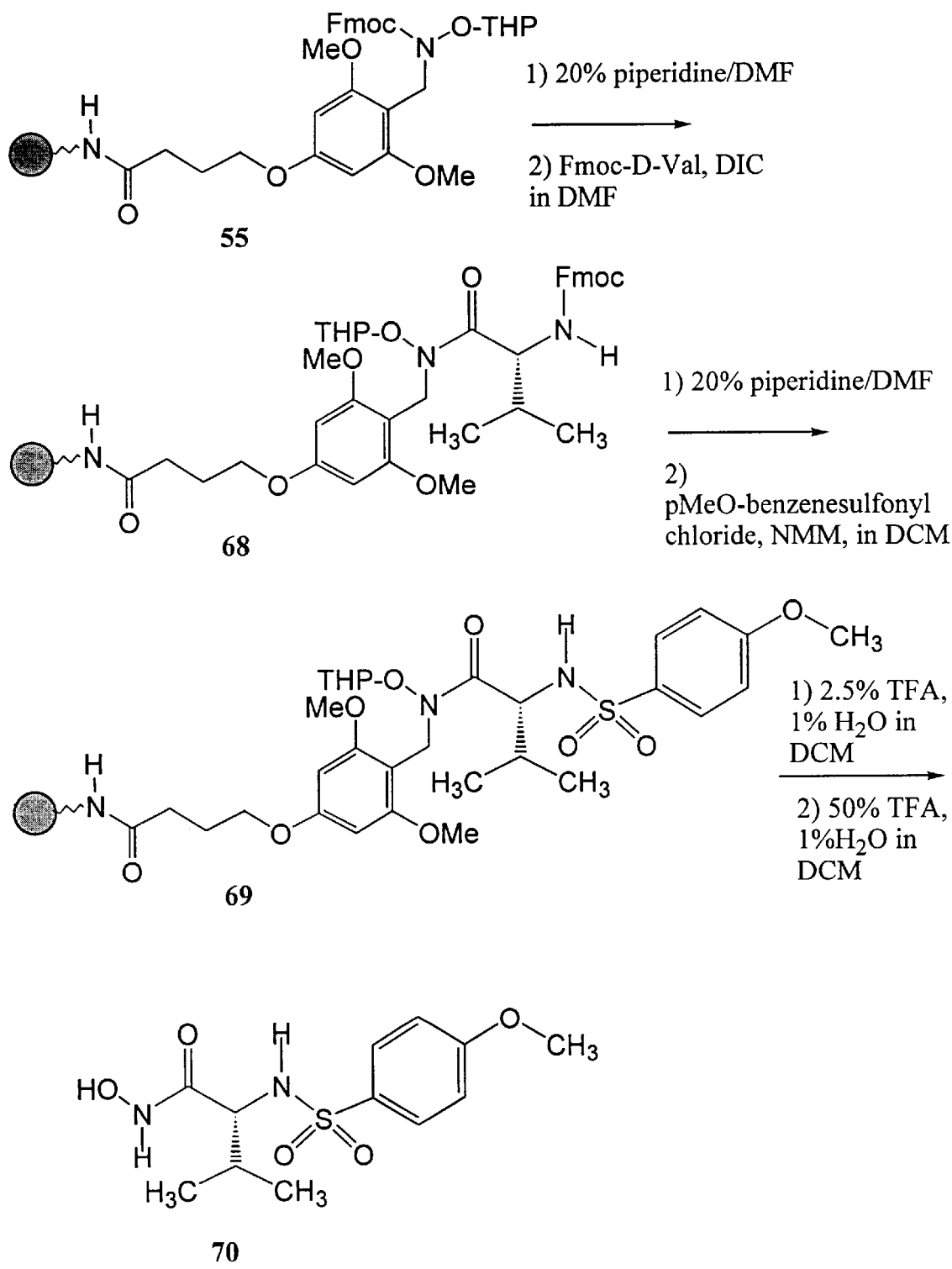
FIG. 7 illustrates a synthetic route to a hydroxylamine compound using the methods of the invention.

Synthesis of Compound 70 (see FIG. 7)

Compound 55 from Example 10 (300 mg) was shaken with 20% piperidine in DMF (5 ml) for 20 min. The resin was washed with MeOH (3×5 ml) and DCM (2×5 ml). Fmoc-D-Valine (203 mg, 10 equiv.) and DIC (diisopropylcarbodiimide) (47 µl, 5 equiv.) were added to the resin in DMF (5 ml) at room temperature under nitrogen. The reaction mixture was shaken for 18 hr. The resin was washed with MeOH (3×5 ml) and DCM (2×5 ml) to yield Compound 68.

Compound 68 (300 mg) was shaken with 20% piperidine in DMF (5 ml) for 20 minutes. The resin was washed with MeOH (3×5 ml) and DCM (2×5 ml). Then N-methylmorpholine (132 µl, 20 equiv.) and 4-methoxybenzenesulfonyl chloride (124 mg, 10 equiv.) in DCM were added to the resin at room temperature and the reaction mixture shaken for 4 hr. The resin was washed with MeOH (3×5 ml) and DCM (2×5 ml) to yield Compound 69.

2.5% TFA, 1% $H_2O$ in DCM (4 ml) was added to the resin and the reaction mixture shaken for 1 hr, followed by washing with MeOH (3×5 ml) and DCM (2×5 ml).

Then 1% $H_2O$, 50% TFA in DCM was added to the resin and the resin shaken for 1 hr. The resin was filtered and the solvent was removed from the filtrate to yield Compound 70. $^1$H NMR: (300 MHz, $CDCl_3$) δ1.05 (d, 6H), 2.18 (m, 1H), 3.81 (s, 3H), 4.29 (m, 1H), 6.98 (d, 2H), 7.77 (d, 2H).

Example 19

Figure 8:
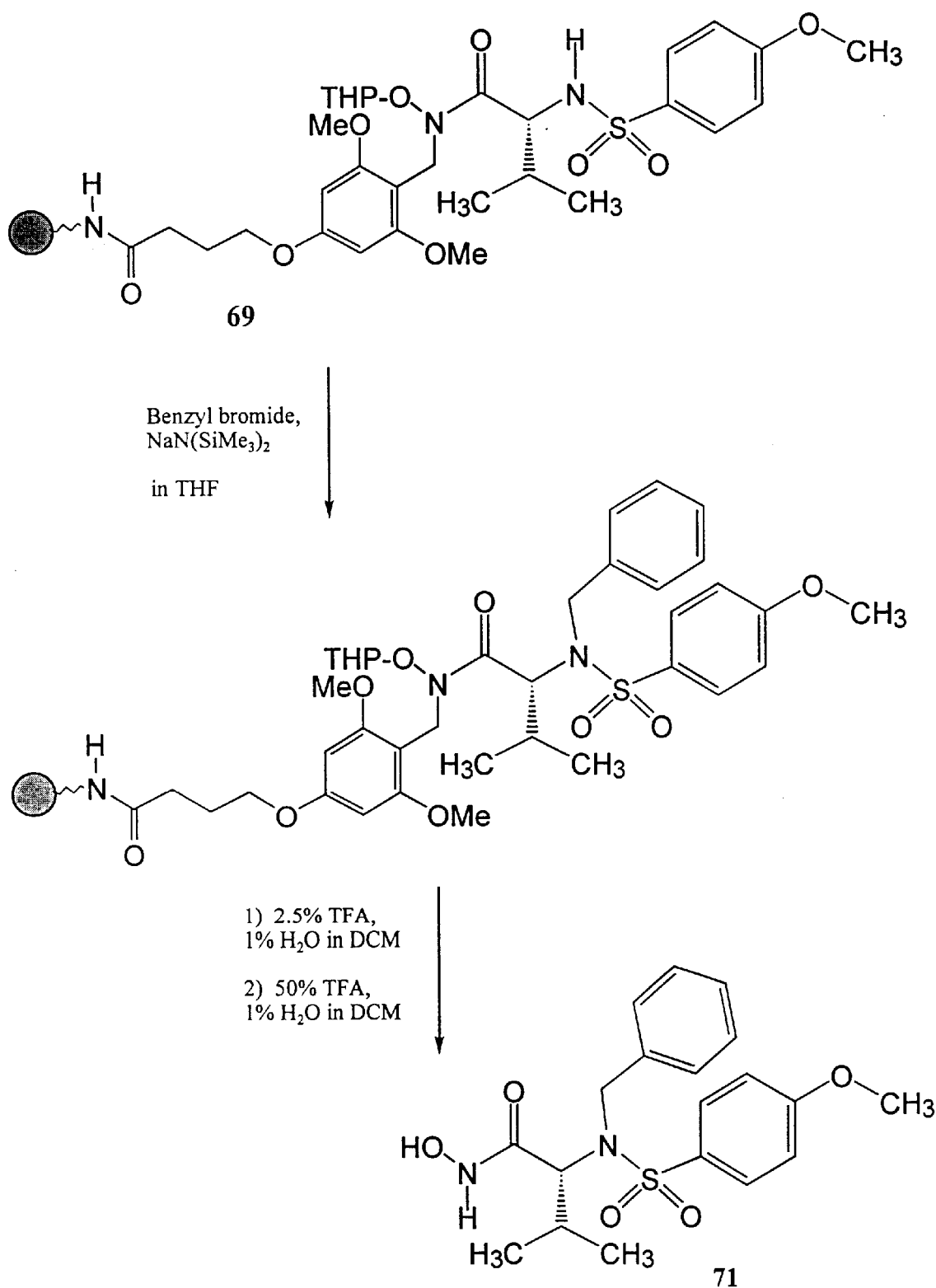
FIG. 8 illustrates a synthetic route to a hydroxylamine compound using the methods of the invention.

Synthesis of Compound 71 (see FIG. 8)

To Compound 69 (300 mg) in THF (5 ml) was added 1 M sodium bis(trimethylsilyl)amide in THF (1.2 ml, 20 equiv.) and benzyl bromide (143 µl, 20 equiv.) at room temperature under argon. The reaction mixture was shaken for 18 hr. The resin was washed with MeOH (3×5 ml) and DCM (2×5 ml). 2.5% TFA, 1% $H_2O$ in DCM (4 ml) was added to the resin and the reaction mixture shaken for 1 hr, followed by washing with MeOH (3×5 ml) and DCM (2×5 ml). Then 1% $H_2O$, 50% TFA in DCM was added to the resin and the resin shaken for 1 hr. The resin was filtered and the solvent was removed from the filtrate to yield Compound 71. $^1$H NMR: (300 MHz, $CDCl_3$) δ1.05 (d, 6H), 2.18 (m, 1H), 3.81 (s, 3H), 4.29 (m, 1H), 5.07 (s, 2H), 6.98 (d, 2H), 7.77 (d, 2H).

Example 20

Figure 9:
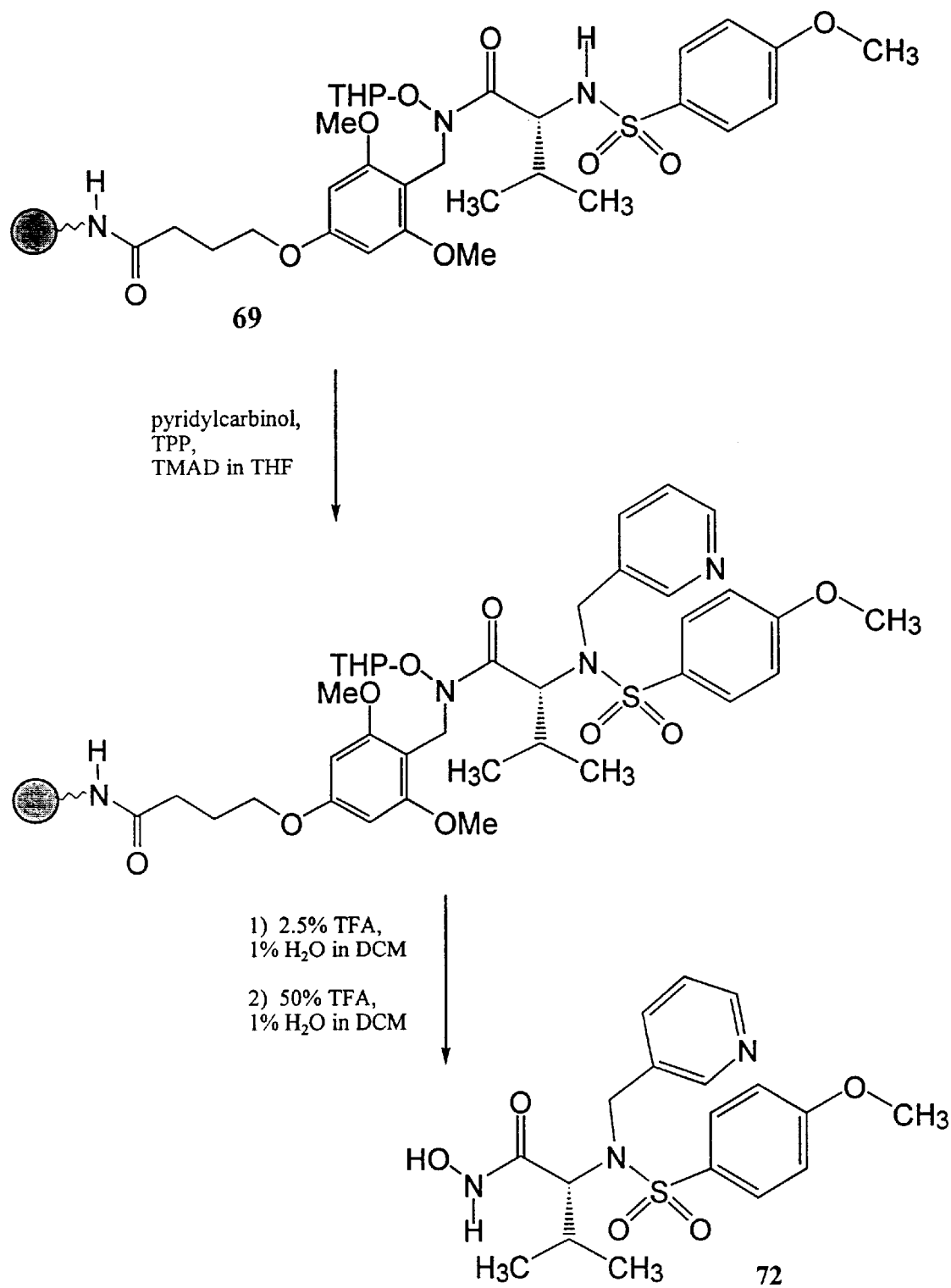
FIG. 9 illustrates a synthetic route to a hydroxylamine compound using the methods of the invention.

Synthesis of Compound 72 (see FIG. 9)

To Compound 69 (300 mg) in THF (4 ml) was added triphenylphosphine (524 mg, 0.5 M), pyridylcarbinol (388 µl, 1.0 M), and diisopropylazodicarboxylate (394 µl, 0.5 M) at room temperature under argon. The reaction was shaken for 18 hr. The resin was washed with MeOH (3×5 ml) and DCM (2×5 ml). 2.5% TFA, 1% $H_2O$ in DCM (4 ml) was added to the resin and the reaction mixture shaken for 1 hr, followed by washing with MeOH (3×5 ml) and DCM (2×5 ml). Then 1% $H_2O$, 50% TFA in DCM was added to the resin and the resin shaken for 1 hr. The resin was filtered and the solvent was removed from the filtrate to yield Compound 72.

Example 21

Figure 10:
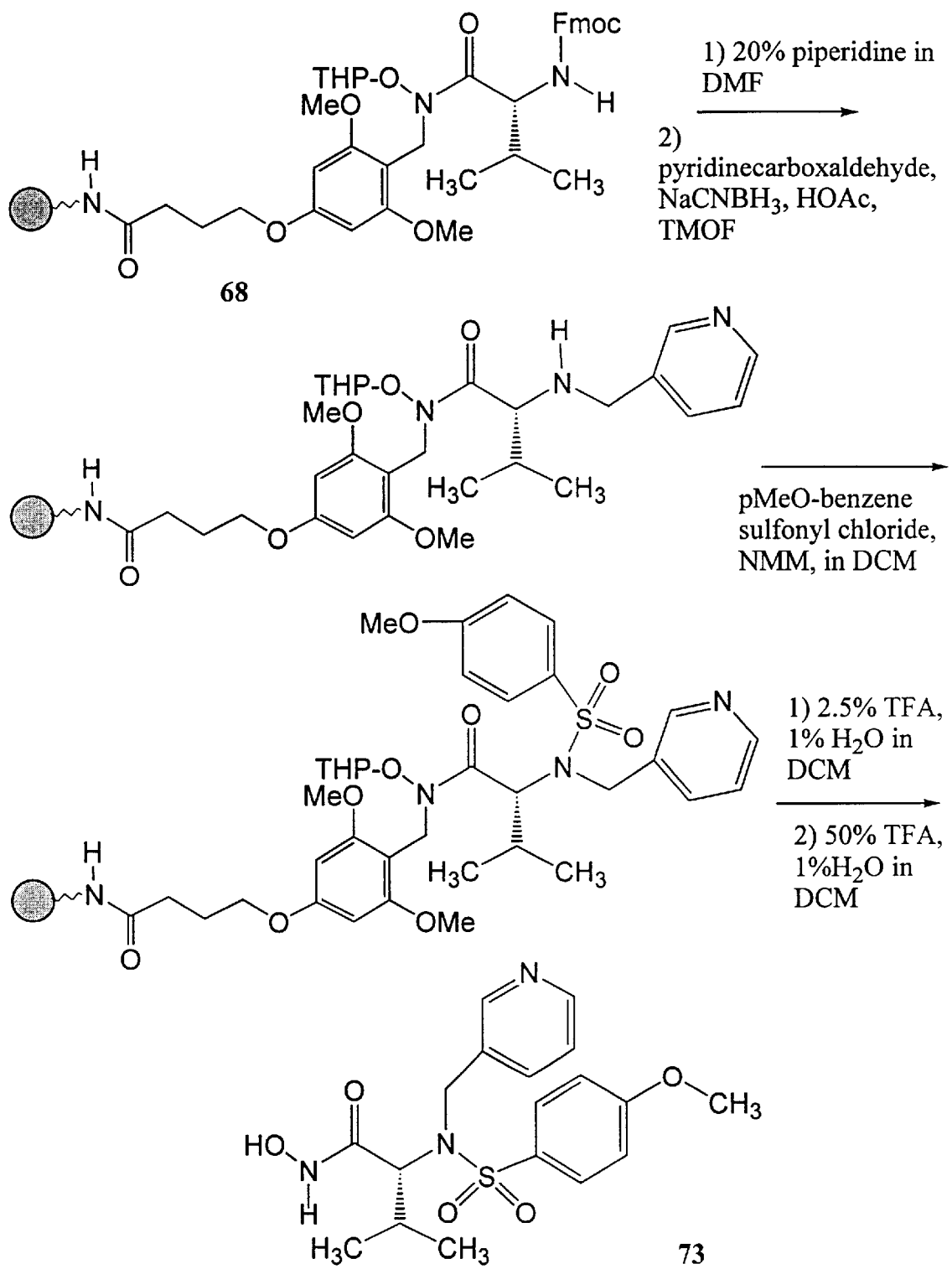
FIG. 10 illustrates a synthetic route to a hydroxylamine compound using the methods of the invention.

Synthesis of Compound 73 (see FIG. 10)

To Compound 68 (300 mg) was added 20% piperidine in DMF (5 ml). The resin was shaken for 20 minutes, then washed with MeOH (3×5 ml) and DCM (2×5 ml). Pyridinecarboxaldehyde (113 µl, 20 equiv.) in trimethyl orthoformate (5 ml) was stirred for 30 min. at room temperature under nitrogen. HOAc (100 µl, 2%) and 1 M $NaCNBH_3$ in THF (1.8 ml, 30 equiv.) were added to the reaction mixture and stirred for 18 hr. The resin was washed with MeOH (3×5 ml) and DCM (2×5 ml).

N-methylmorpholine (132 µl, 20 equiv.) and 4-methoxybenzene sulfonyl chloride (124 mg, 10 equiv.) were added to the resin at room temperature. The reaction was shaken for 4 hr. and the resin washed with MeOH (3×5 ml) and DCM (2×5 ml).

2.5% TFA, 1% $H_2O$ in DCM (4 ml) was added to the resin and the reaction mixture shaken for 1 hr, followed by washing with MeOH (3×5 ml) and DCM (2×5 ml). Then 1% $H_2O$, 50% TFA in DCM was added to the resin and the resin shaken for 1 hr. The resin was filtered and the solvent was removed from the filtrate to yield Compound 73.

Note that as Compound 72 and Compound 73 are identical, the above Example 21 illustrates an alternate synthetic route to the synthesis used in Example 20.

Example 22

Use of O-Allyl protected hydroxylamine resin in solid-phase synthesis and solid-phase combinatorial synthesis The O-allyl protected hydroxylamine resin (Compound 65) can be derivatized in analogous fashion as the O-THP protected resin in the previous examples. However, after derivatization is complete, the compounds are cleaved from the resin by using 1% $H_2O$, 50% TFA in DCM. The O-allyl protecting group is not removed by this procedure. To remove the O-allyl protecting group, $Pd(PPh_3)_4$/$PPh_3$/pyrrolidine in acetonitrile is used (where $PPh_3$ is triphenylphosphine).

Alternatively, the allyl group can be removed while the compounds are still attached to the resin, by treating the resin with $Pd(PPh_3)_4$/$PPh_3$/pyrrolidine in acetonitrile. The compounds can then be removed from the resin by using 1% $H_2O$, 50% TFA in DCM.

Example 23

Synthesis of a combinatorial library of hydroxylamine compounds

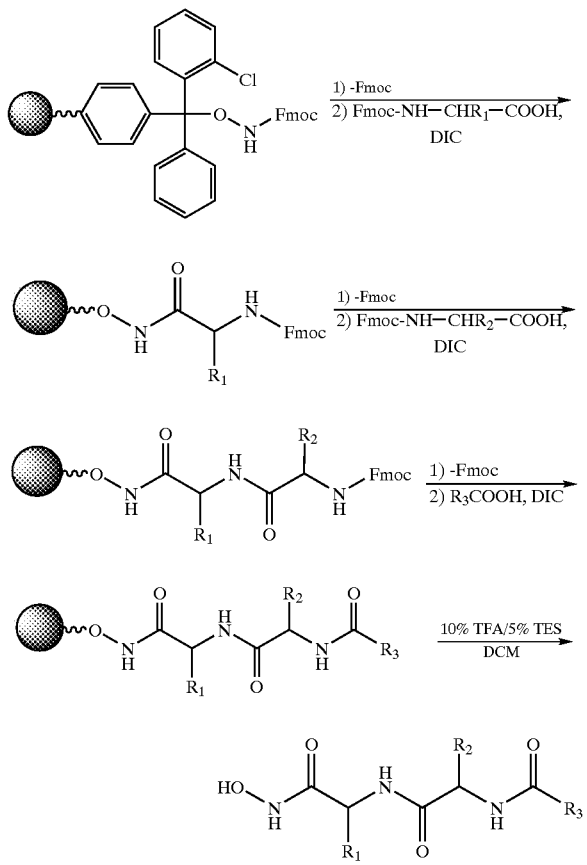

Generation of a combinatorial library can be accomplished by the reaction scheme outline above, either by 1) utilizing a mixture of amino acid reagents at each step in the synthesis; 2) using the "split and pool" method to react resin portions with different reagents and recombining; or 3) synthesizing small number of compounds separately, then combining the compounds at the end of the procedure to form the library. While the reaction scheme depicts amino acids, imino acids including, but not limited to, Fmoc-L-proline and Fmoc-D-proline can be used as well.

N-Fmoc-hydroxylamine 2-chlorotrityl resin (Novabiochem, San Diego, Calif.) (100 mg, 0.75 mmol/g) is shaken for 2 hr. in a solution of 20% piperidine in DMF (2 ml). The reaction is washed with MeOH (2×2 ml) and DCM (3×2 ml). Then the Fmoc amino acid, Fmoc-NH—CH ($R_1$)—COOH (10 equiv) and DIC (5 equiv) are added to the resin in DMF (2 ml), and the reaction mixture is shaken for 18 hr. The reaction mixture is washed with MeOH (2×2 ml) and DCM (3×2 ml). A solution of 20% piperidine in DMF (2 ml) is added to the resin and shaken for 45 min.; the resin is then washed with MeOH (2×2 ml) and DCM (3×2 ml). Then the Fmoc amino acid Fmoc-NH—CH($R_2$)—COOH (10 equiv) and DIC (5 equiv) are added to the resin in DMF (2 ml), and the reaction mixture shaken for 18 hr. The reaction mixture is washed with MeOH (2×2 ml) and DCM (3×2 ml). A solution of 20% piperidine in DMF (2 ml) is added to the resin and shaken for 20 min; the resin is then washed with MeOH (2×2 ml) and DCM (3×2 ml). $R_3$COOH (10 equiv) and DIC (5 equiv) are added to the resin in DMF (2 ml), and the reaction mixture shaken for 18 hr. The reaction mixture is washed with MeOH (2×2 ml) and DCM (3×2 ml). A solution of 10% TFA, 5% TES in DCM is added to reaction and shaken for 30 min, filtered, and the filtrate is concentrated under reduced pressure.

Example 24

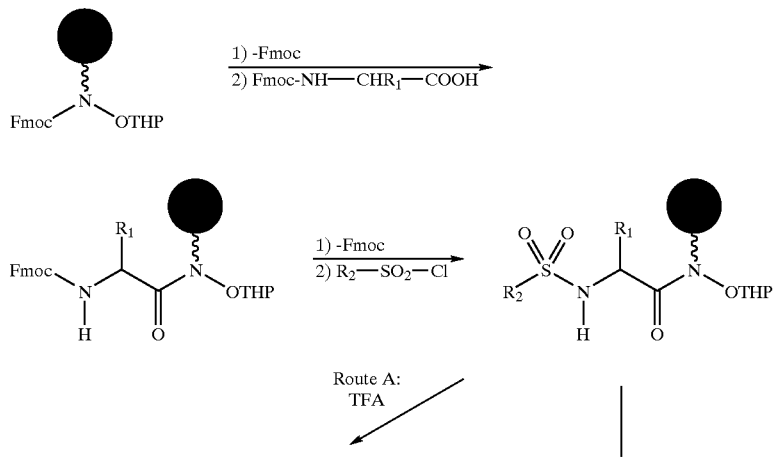

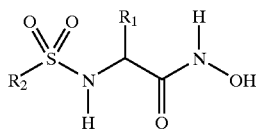

Route B:
1) TMAD, TBP, pyridylcarbinol
2) TFA

Route C:
1) DMF, CH3I, phosphazene
2) TFA

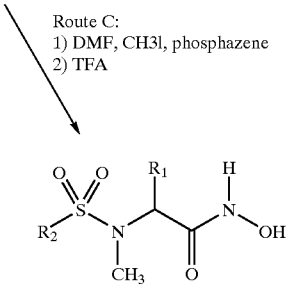

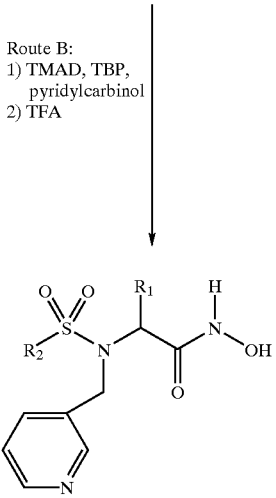

The sulfonamide nitrogen of the compounds in the figure above can be derivatized by using Route B (which attaches a pyridylmethyl group) or Route C (which attaches a methyl group), or left underivatized by using Route A. Route B is described in Steps 3 and 4 of Example 6. Route A is described in Step 4 of Example 6. Route C is described as follows: iodomethane (10 equiv) was added to a solution of t-butylimino-tri(pyrrolidino) phosphorane (phosphazene base P$_1$-t-Bu-tris(tetramethylene), Fluka, Ronkonkoma, N.Y.) (20 equiv) and resin (100 mg) in DMF (2 ml). The reaction mixture was shaken for 18 hr. and the resin was filtered and washed sequentially with MeOH (3×5 ml) and DCM (2×5 ml). A solution of 2.5% TFA and 1% H$_2$O in DCM (4 ml) was then added, and the mixture was shaken for 1 h. The resin was filtered and washed sequentially with MeOH (3×5 ml) and DCM (2×5 ml). A solution of 50% TFA and 1% H$_2$O in DCM (4 ml) was then added, the mixture shaken for 1 h, filtered, and the filtrate was concentrated under reduced pressure.

By utilizing various reagents for Fmoc-NH—CHR$_1$—COOH and R$_2$—SO$_2$—Cl, and by utilizing Routes A, B and C as described above, a combinatorial library can be synthesized.

Example 25

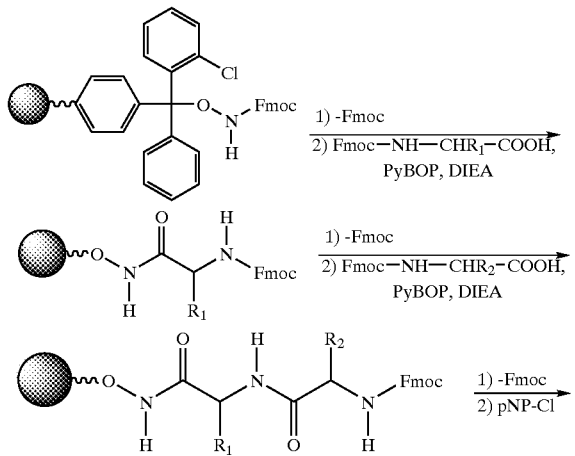

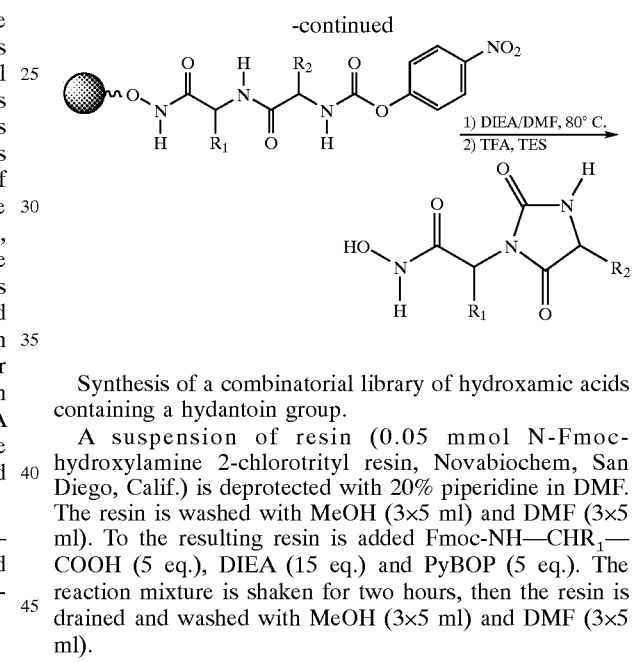

Synthesis of a combinatorial library of hydroxamic acids containing a hydantoin group.

A suspension of resin (0.05 mmol N-Fmoc-hydroxylamine 2-chlorotrityl resin, Novabiochem, San Diego, Calif.) is deprotected with 20% piperidine in DMF. The resin is washed with MeOH (3×5 ml) and DMF (3×5 ml). To the resulting resin is added Fmoc-NH—CHR$_1$—COOH (5 eq.), DIEA (15 eq.) and PyBOP (5 eq.). The reaction mixture is shaken for two hours, then the resin is drained and washed with MeOH (3×5 ml) and DMF (3×5 ml).

The resin is then deprotected with 20% piperidine in DMF. The resin is washed with MeOH (3×5 ml) and DMF (3×5 ml). To the resulting resin is added Fmoc-NH—CHR$_2$—COOH (5 eq.), DIEA (15 eq.) and PyBOP (5 eq.). The reaction mixture is shaken for two hours, then the resin is drained and washed with MeOH (3×5 ml) and DMF (3×5 ml).

The resin is then deprotected with 20% piperidine in DMF. The resin is washed with MeOH (3×5 ml) and DMF (3×5 ml).

DIEA (10 equiv.) in THF is then added to the resin. Subsequently, 4-nitrophenyl chloroformate (p-NP-Cl) (5 eq.) is added. The reaction mixture is shaken for 18 hours at RT; then the resin is washed with DMF (2×5 mL) and DCM (3×5 mL).

A solution of 10% DIEA in DMF is added to the resin and the mixture is heated at 80° C. overnight. Then the resin is washed with MeOH (2×5 ml) and DCM (3×5 ml).

A solution of 10% TFA and 5% triethylsilane (TES) in DCM (4 mL) is then added to the resin and the reaction mixture is shaken for 30 minutes. The resin is filtered; the filtrate is collected and the solvent evaporated under reduced pressure to yield the product hydantoin.

By introducing a variety of amino acids at the steps where Fmoc-NH—$CHR_1$—COOH and Fmoc-NH—$CHR_2$—COOH are coupled to the resin (for example, by using a cocktail of amino acids at each step; by splitting the resin, reacting single amino acids separately, and recombining the resin; or by synthesizing compound discretely and mixing them together) a combinatorial library of hydroxylamine compounds containing a hydantoin moiety is synthesized.

All references, publications and patents mentioned herein are hereby incorporated by reference herein in their entirety.

Although the forgoing invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims.

What is claimed is:

1. A method for the synthesis of a library comprising a plurality of hydroxylamine and/or hydroxylamine derivative compounds, comprising the steps of coupling a hydroxylamine or hydroxylamine derivative comprising an O-protecting group to a solid support to form a solid support-bound O-protected hydroxylamine or hydroxylamine derivative;

derivatizing the solid support bound O-protected hydroxylamine or hydroxylamine derivative by either introducing a mixture of reagents that react with said O-protected hydroxylamine or hydroxylamine derivative, or by reacting portions of the solid support-bound O-protected hydroxylamine or hydroxylamine derivative with different reagents that react with the O-protected hydroxylamine or hydroxylamine derivative and recombining said portions;

cleaving the derivatized O-protected hydroxylamine or hydroxylamine derivatives from the solid support;

and removing the O-protecting group.

2. The method of claim 1, where the step of preparing a solid support-bound O-protected hydroxylamine or hydroxylamine derivative comprises adding an O-protected hydroxylamine or hydroxylamine derivative to a solid support comprising a leaving group, thereby displacing the leaving group from the solid support to produce a solid support-bound O-protected hydroxylamine or hydroxylamine derivative.

3. The method of claim 1, where the step of preparing a solid support-bound O-protected hydroxylamine or hydroxylamine derivative comprises adding an O-protected hydroxylamine or hydroxylamine derivative bound to a linker group to a solid support bearing an amine group to produce a solid support-bound O-protected hydroxylamine or hydroxylamine derivative.

4. The method of claim 1, wherein the hydroxylamine and hydroxylamine derivative containing compounds are selected from the group consisting of hydroxylamines.

5. The method of claim 1, wherein the O-protected hydroxylamine or hydroxylamine derivative is selected from the group consisting of O-trityl hydroxylamine, O-(t-butyldimethylsilyl)hydroxylamine, O-allyl hydroxylamine, O-benzyl hydroxylamine, O-(4-methoxybenzyl) hydroxylamine, O-(2,4-dimethoxybenzyl)hydroxylamine, and O-(2-tetrahydropyranyl)hydroxylamine.

6. The method of claim 2, wherein the leaving group is selected from the group consisting of bromide, iodide, and mesylate.

7. The method of claim 2, wherein the solid support comprising a leaving group is bromomethylphenoxy resin.

* * * * *